US007947270B2

(12) United States Patent
Franklin

(10) Patent No.: US 7,947,270 B2
(45) Date of Patent: May 24, 2011

(54) REMOVING DENTAL PLAQUE WITH KRILL ENZYMES

(75) Inventor: Richard L. Franklin, London (GB)

(73) Assignee: Arcimboldo AB, Stockholm (SE)

( * ) Notice: Subject to any disclaimer, the term of this patent is extended or adjusted under 35 U.S.C. 154(b) by 929 days.

(21) Appl. No.: 10/750,184

(22) Filed: Dec. 31, 2003

(65) Prior Publication Data

US 2005/0025722 A1 Feb. 3, 2005

Related U.S. Application Data

(60) Continuation of application No. 09/549,642, filed on Apr. 14, 2000, now abandoned, which is a division of application No. 09/303,375, filed on Apr. 30, 1999, now abandoned, which is a division of application No. 08/600,273, filed on Feb. 8, 1996, now Pat. No. 5,958,406, which is a continuation-in-part of application No. 08/486,820, filed on Jun. 7, 1995, now Pat. No. 6,030,612, which is a continuation-in-part of application No. 08/385,540, filed on Feb. 8, 1995, now Pat. No. 5,945,102, which is a continuation-in-part of application No. 08/338,501, filed as application No. PCT/SE93/00455 on May 21, 1993, now abandoned.

(30) Foreign Application Priority Data

May 22, 1992 (SE) ........................ 9201628

(51) Int. Cl.
*A61K 38/46* (2006.01)
*A61K 38/54* (2006.01)
*C12N 9/00* (2006.01)
(52) U.S. Cl. ..................... 424/94.64; 435/183
(58) Field of Classification Search .................. None
See application file for complete search history.

(56) References Cited

U.S. PATENT DOCUMENTS

| | | | |
|---|---|---|---|
| 4,677,069 A | 6/1987 | Chen et al. | |
| 4,801,451 A | 1/1989 | Hellgren et al. | |
| 4,837,009 A * | 6/1989 | Ractliff | 424/53 |
| 4,963,491 A | 10/1990 | Hellgren et al. | |
| 5,134,119 A | 7/1992 | Lezdey John et al. | |
| 5,439,935 A | 8/1995 | Rawlings et al. | |
| 5,945,102 A | 8/1999 | de Faire et al. | |
| 5,958,406 A | 9/1999 | de Faire et al. | |
| 6,030,612 A | 2/2000 | de Faire et al. | |
| 2006/0134641 A1 | 6/2006 | Franklin | |

FOREIGN PATENT DOCUMENTS

| | | |
|---|---|---|
| EP | 0170115 | 7/1985 |
| EP | 0 257 003 * | 2/1988 |
| WO | 9319732 | 10/1993 |
| WO | 9324142 | 12/1993 |
| WO | 9419005 | 9/1994 |
| WO | 9507686 | 3/1995 |
| WO | 9507688 | 3/1995 |

OTHER PUBLICATIONS

Definitions for Glycosaminoglycan and Glucosaminoglycan, On-Line Medical Dictionary, CancerWEB 1997-2002.*
Rathgeber WF, S. Afr. Med. J., (45(7):181-183 (1971) [English].
Coblentz, J. Am. Geriatr Soc., 16(9):1039-1046 (1968) [English].
Grant and Eisen, Substrate Specificity of the Collagenolytic Serine Protease from Uca Pugilator: Studies with Noncollagegenous Substrates, Biochemistry, 19:6089-6095 (1980).
Grant et al., Collagenolytic Protease from Fiddler Crab (Uca Pugilator), Methods in Enzymology, 80:722-734 (1980).
Grant et al., A Collagenolytic Serine Protease with Trypsin-Like Specificity from the Fiddler Crab Uca Pugilator, Biochemistry, 22:354-358 (1983).
Welgus and Grant, Degradation of Collagen Substrates by a Trypsin-Like Serine Protease from the Fiddler Crab Uca Pugilator, Biochemistry, 22:2228-2233 (1983).
Al-Mohanna et al., Mitotic E- and Secretory F-Cells in the Hepatopancreas of the Shrimp Penaeus Semisulcatus (Crustacea: Decapoda), J. Mar. Biol. Ass. U.K., 65:901-910 (1985).
Lipman and Pearson, Rapid and Sensitive Protein Similarity Searches, Science, 227:1435-1441 (Mar. 22, 1985).
Gudmundsodottir et al., Isolation and Characterization of cDNAS from Atlantic Cod Encoding Two Different Forms of Trypsinogen, Eur. J. Biochem., 217, 1091-1097 (1993).
Lu et al., The Midgut Trypsins of Shrimp (Penaeus Monodon), Biol. Chem. Hoppe-Seyler, 371:851-859 (Sep. 1990).
Turkiewicz et al., Collagenolytic Serine Proteinase from Euphausia Superba Dana (Antarctic Krill), Comp. Biochem. Physiol., 99B:359-371 (1991).
Tsai et al., The Midgut Chymotrypsins of Shrimps (Penaeus Monodon, Penaeus Japonicus and Penaeus Penicillatus) Biochimica et Biophysica Acta, 1080:59-67 (1991).
Wormhoudt et al., Purification, Biochemical Characterization and N-Terminal Sequence of a Serine-Protease with Chymotrypsic and Collagenolytic Activities in a Tropical Shrimp, Penaeus Vannamei (Crustacea, Decapoda), Comp. Biochem. Physiol., 103B(3):675-680 (1992).
Sellos and Wormhoudt, Molecular Cloning of a cDNA that Encodes a Serine Protease with Chymotryptic and Collagenolytic Activities in the Hepatopancreas of the Shrimp Penaeus Vanameii (Crustacea, Decapoda), FEBS, 309 (3):219-224 (Sep. 1992).

(Continued)

*Primary Examiner* — Bo Peng
(74) *Attorney, Agent, or Firm* — Knoble Yoshida & Dunleavy, LLC

(57) ABSTRACT

The invention relates to a multifunctional enzyme that can be derived from crustaceans or fish. The enzyme has at least one of a chymotrypsin, trypsin, elastase, collagenase and exo peptidase activity, and a molecular weight between about 20 kd and about 40 kd as determined by SDS PAGE. Preferably, the multifunctional enzyme has substantial anti cell-cell adhesion activity. Preferably, the multifunctional enzyme has substantial homology with the krill multifunctional enzyme. These enzymes are useful for treating viral infections such as herpes outbreaks, fungal, bacterial or parasitic infections, including the primary and secondary infections of leprosy, colitis, ulcers, hemorrhoids, corneal scarring, dental plaque, acne, cystic fibrosis, blood clots, wounds, immune disorders including autoimmune disease and cancer. Additionally, the invention relates to a method of purifying the multifunctional enzyme, and to a preparation of essentially purified multifunctional enzyme.

20 Claims, 11 Drawing Sheets

OTHER PUBLICATIONS

Klimova et al., The Isolation and Properties of Collagenolytic Proteases from Crab Hepatopancreas, Biochemical and Biophysical Research Communications, 166(3):1411-1420 (Feb. 1990).

Tsu et al., The Substrate Specificity of Uca Pugilator Collagenolytic Serine Protease 1 Correlates with the Bovine Type I Collagen Cleavage Sites, The Journal of Biochemical Chemistry, 269(30)19565-19572 (1994).

A. Bucht et al., Immunological Characterization of Three Highly Purified Trypsin-Like Enzymes from Antarctic Krill (Euphausia Superba), Biol. Chem. Hoppe Sryler, 367:366, Abstract 06.03.55 (1986).

Turkiewicz et al., Purification and Characterization of a Proteinase from Euphausia Superba Dana (Antarctic Krill), Acta Biochimica Polonica, 33(2):87-89 (1986).

Chen et al., Purification and Properties of Trypsin-Like Enzymes and a Carboxypeptidase A From Euphausia Superba, Journal of Food Biochemistry, 2:349-366 (1978).

Kimoto et al., Purification and Characterization of Serine Proteinases from Euphasia Superba, Agric. Biol. Chem., 47 (3):529-534 (1983).

Knut Kr. Osnes et al., On the Purification and Characterization of Three Anoinic, Serine-Type Peptide Hydrolases from Antarctic Krill, Euphausia Superba, Comp. Biochem. Physiol., 82B(4):607-619 (1995).

Knut Kr. Osnes et al., On the Purification and Characterization of Exopeptidases from Antarctic Krill, Euphausia Superba, Comp. Biochem. Physiol., 83B(2):445-458 (1986).

Knut Kr. Osnes et al., Hydrolysis of Proteins by Peptide Hydrolases of Antarctic Krill, Euphausia Superba, Comp. Biochem. Physiol., 83B(4):801-805, (1986).

Knut Kr. Osnes et al., Peptide Hydrolases of Antarctic Krill, Euphausia Superba, Comp. Biochem. Physiol, 82B (4):599-606, (1985).

Olav Seather et al., Proteolysis Post Mortem in North Atlantic Krill, Comp. Biochem. Physical, 88B(1):165-176 (1987).

J. Melrose et al., Evauation of Digestive Proteinases from the Antarctic Krill Euphausia Superba, as Potential Chemonucleolytic Agents, Arch Orthop Trauma Surg., 114:145-152 (1995).

Y. Sakharov, Potent Debriding Ability of Collagenolytic Protease Isolated from the Hepatopancreas of the King Crab Paralithodes Camtschatica, Arch Dermatol Res., 285:32-35 (1993).

Arthur Z. Eisen, A Collagenolytic Protease from the Hepatopancreas of the Fiddler Crab, UCA Pugilator, Purification and Properties, Biochemistry, 12(9):1814-1822 (1973).

Asuncion Olalla et la:, Purification and Properties of Three Proteases from the Larvae of the Brine Shrimp Artemia Salina, Biochimica et Biophysica Acta, 523:181-190 (1978).

Spindler et al., Partial Characterization of Chitin Degrading Enzymes from Two Euphausiids, Euphausia Superba, and Meganyctiphanes Norvegica, Polar Biology, 9:115-122 (1988).

Karlstam and Ljunglof, Detection and Partial Purification of a Hyaluronic Acid-Degrading Enzyme from Antarctic Krill (Euphausia Superba, ), Biol. Chem. Hoppe Seyler, 367:339 (1986).

Kimoto et al., Acid Proteinases from Antarctic Krill, Euphausia Superba: Partial Purification and Some Properties, Journal of Food Science, 46:1881-1884 (1981).

Kraft and Falkenberg, Biol. Chem. Hoppe Seyler, 353:1540-1541 (1972).

Sakharov et al., Purification and Characterization of Two Serine Collagenolytic Proteases from Crab Paralithodes Camtschatica, Comp. Biochem. Physiol., 108B:561-568 (1994).

Gates et al., Isolation of Comparative Properties of Shrimp Trypsin, Shrimp Trypsin, 8(11):4483-4489 (1969).

Jacobs, J Am Podiatry Assoc., 55(11):743-746 (1965) [English].

Goodfriend, J Am Podiatry Assoc., 55(9):667-669 (1965) [English].

* cited by examiner

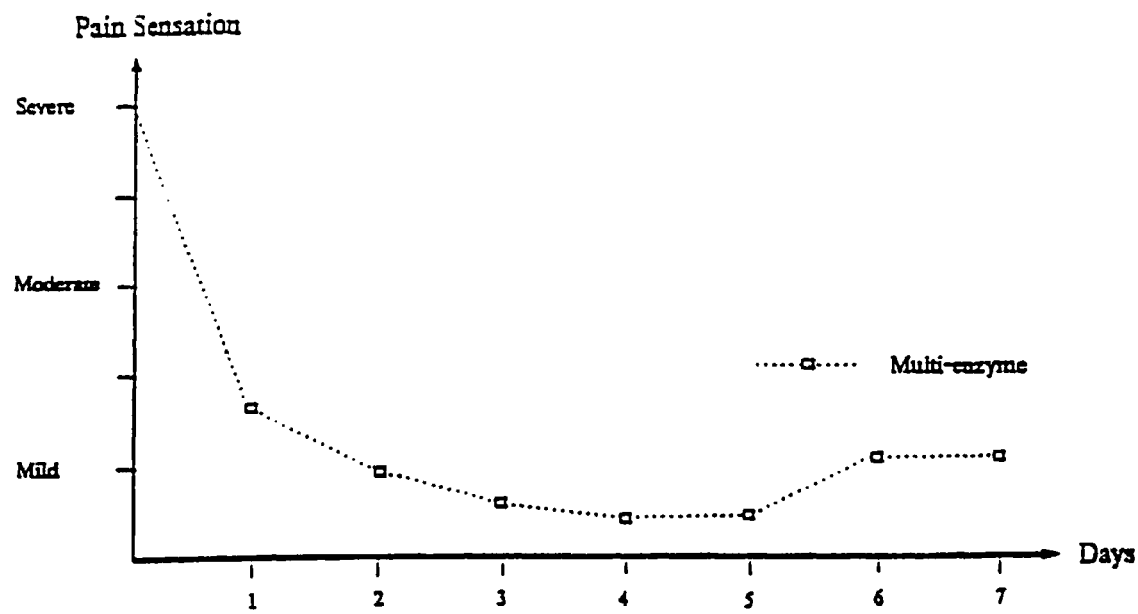
FIG. 11 Average Pain Relief scoring over 7 days scoring with Multi-enzyme preparations from Krill
Definitions
Severe Pain: Horse is not supporting itself on painful leg.
Moderate Pain: Horse is from time to time supporting itself on painful leg, more than 30 seconds each time.
Mild Pain: Horse is continously supporting itself on painful leg, more than 2 minutes each time.

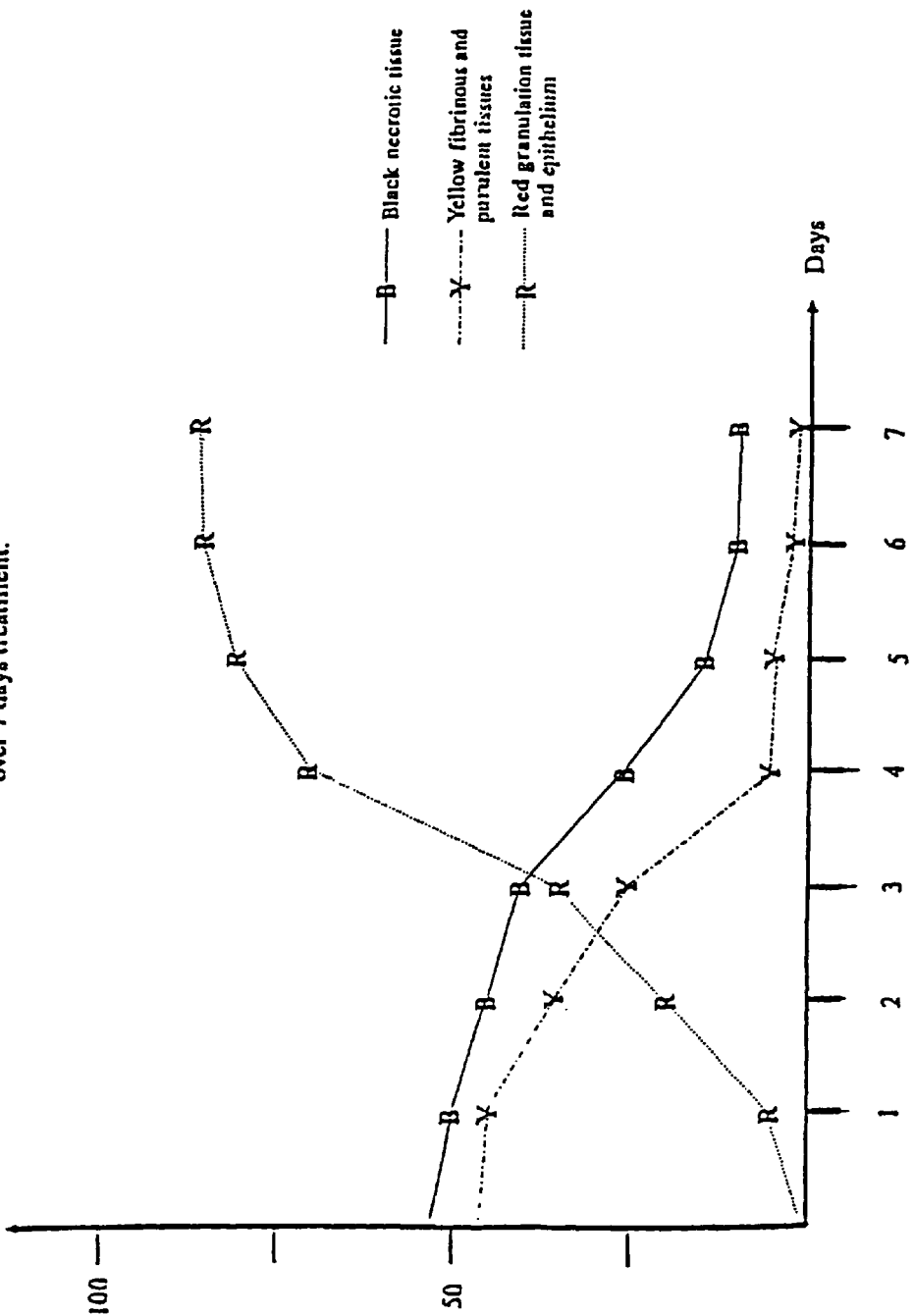
FIG. 12 Decomposing efficacy of Single-enzyme preparation from Krill on necroses, fibrin, pus, and blood clots over 7 days treatment.

SEQUENCE LISTING

```
<160> NUMBER OF SEQ ID NOS: 20

<210> SEQ ID NO 1
<211> LENGTH: 25
<212> TYPE: PRT
<213> ORGANISM: Euphasia superba

<400> SEQUENCE: 1

Ile Val Gly Gly Asn Glu Val Thr Pro His Ala Tyr Pro Trp Gln Val
 1               5                  10                  15

Gly Leu Phe Ile Asp Asp Met Tyr Phe
            20                  25

<210> SEQ ID NO 2
<211> LENGTH: 25
<212> TYPE: PRT
<213> ORGANISM: Euphasia superba

<400> SEQUENCE: 2

Ile Val Gly Gly Met Glu Val Thr Pro His Ala Tyr Pro Trp Gln Val
 1               5                  10                  15

Gly Leu Phe Ile Asp Asp Met Tyr Phe
            20                  25

<210> SEQ ID NO 3
<211> LENGTH: 25
<212> TYPE: PRT
<213> ORGANISM: Penaeus vanameii
```

```
<400> SEQUENCE: 3

Ile Val Gly Gly Val Glu Ala Thr Pro His Ser Trp Pro His Gln Ala
1               5                   10                  15

Ala Leu Phe Ile Asp Asp Met Tyr Phe
            20                  25

<210> SEQ ID NO 4
<211> LENGTH: 20
<212> TYPE: PRT
<213> ORGANISM: Penaeus vanameii
<220> FEATURE:
<221> NAME/KEY: VARIANT
<222> LOCATION: (1)...(20)
<223> OTHER INFORMATION: Xaa = Any Amino Acid

<400> SEQUENCE: 4

Ile Val Gly Gly Val Glu Ala Thr Pro His Ser Xaa Pro His Gln Ala
1               5                   10                  15

Ala Leu Phe Ile
            20

<210> SEQ ID NO 5
<211> LENGTH: 25
<212> TYPE: PRT
<213> ORGANISM: Penaeus monodon

<400> SEQUENCE: 5

Ile Val Gly Gly Thr Ala Val Thr Pro Gly Glu Phe Pro Tyr Gln Leu
1               5                   10                  15

Ser Phe Gln Asp Ser Ile Glu Gly Val
            20                  25

<210> SEQ ID NO 6
<211> LENGTH: 25
<212> TYPE: PRT
<213> ORGANISM: Penaeus monodon

<400> SEQUENCE: 6

Ile Val Gly Gly Val Glu Ala Val Pro Gly Val Trp Pro Tyr Gln Ala
1               5                   10                  15

Ala Leu Phe Ile Ile Asp Met Tyr Phe
            20                  25

<210> SEQ ID NO 7
<211> LENGTH: 25
<212> TYPE: PRT
<213> ORGANISM: Penaeus monodon

<400> SEQUENCE: 7

Ile Val Gly Gly Val Glu Ala Val Pro His Ser Trp Pro Tyr Gln Ala
1               5                   10                  15

Ala Leu Phe Ile Ile Asp Met Tyr Phe
            20                  25

<210> SEQ ID NO 8
<211> LENGTH: 25
<212> TYPE: PRT
<213> ORGANISM: Uca pugilator

<400> SEQUENCE: 8

Ile Val Gly Gly Val Glu Ala Val Pro Asn Ser Trp Pro His Gln Ala
1               5                   10                  15
```

```
Ala Leu Phe Ile Asp Asp Met Tyr Phe
            20              25

<210> SEQ ID NO 9
<211> LENGTH: 20
<212> TYPE: PRT
<213> ORGANISM: Uca pugilator

<400> SEQUENCE: 9

Ile Val Gly Gly Gln Asp Ala Thr Pro Gly Gln Phe Pro Tyr Gln Leu
1               5                   10                  15

Ser Phe Gln Asp
            20

<210> SEQ ID NO 10
<211> LENGTH: 19
<212> TYPE: PRT
<213> ORGANISM: King crab
<220> FEATURE:
<221> NAME/KEY: VARIANT
<222> LOCATION: (1)...(19)
<223> OTHER INFORMATION: Xaa = Any Amino Acid

<400> SEQUENCE: 10

Ile Val Gly Gly Gln Glu Ala Ser Pro Gly Ser Trp Pro Xaa Gln Val
1               5                   10                  15

Gly Leu Phe

<210> SEQ ID NO 11
<211> LENGTH: 20
<212> TYPE: PRT
<213> ORGANISM: Kamchatka crab
<220> FEATURE:
<221> NAME/KEY: VARIANT
<222> LOCATION: (1)...(20)
<223> OTHER INFORMATION: Xaa = Any Amino Acid

<400> SEQUENCE: 11

Ile Val Gly Gly Gln Glu Ala Ser Pro Gly Ser Trp Pro Xaa Gln Val
1               5                   10                  15

Gly Leu Phe Phe
            20

<210> SEQ ID NO 12
<211> LENGTH: 20
<212> TYPE: PRT
<213> ORGANISM: Kamchatka crab

<400> SEQUENCE: 12

Ile Val Gly Gly Thr Glu Val Thr Pro Gly Glu Ile Pro Tyr Gln Leu
1               5                   10                  15

Ser Leu Gln Asp
            20

<210> SEQ ID NO 13
<211> LENGTH: 20
<212> TYPE: PRT
<213> ORGANISM: Kamchatka crab

<400> SEQUENCE: 13

Ile Val Gly Gly Thr Glu Val Thr Pro Gly Glu Ile Pro Tyr Gln Leu
1               5                   10                  15

Ser Phe Gln Asp
            20
```

```
<210> SEQ ID NO 14
<211> LENGTH: 20
<212> TYPE: PRT
<213> ORGANISM: Kamchatka crab
<220> FEATURE:
<221> NAME/KEY: VARIANT
<222> LOCATION: (1)...(20)
<223> OTHER INFORMATION: Xaa = Any Amino Acid

<400> SEQUENCE: 14

Ile Val Gly Gly Ser Glu Ala Thr Ser Gly Gln Phe Pro Tyr Gln Xaa
 1               5                  10                  15

Ser Phe Gln Asp
            20

<210> SEQ ID NO 15
<211> LENGTH: 20
<212> TYPE: PRT
<213> ORGANISM: Crayfish

<400> SEQUENCE: 15

Ile Val Gly Gly Thr Asp Ala Thr Leu Gly Glu Phe Pro Tyr Gln Leu
 1               5                  10                  15

Ser Phe Gln Asn
            20

<210> SEQ ID NO 16
<211> LENGTH: 20
<212> TYPE: PRT
<213> ORGANISM: Bovine

<400> SEQUENCE: 16

Ile Val Asn Gly Glu Asp Ala Val Pro Gly Ser Trp Pro Trp Gln Val
 1               5                  10                  15

Ser Leu Gln Asp
            20

<210> SEQ ID NO 17
<211> LENGTH: 25
<212> TYPE: PRT
<213> ORGANISM: Salmon

<400> SEQUENCE: 17

Ile Val Gly Gly Tyr Glu Cys Lys Ala Tyr Ser Gln Ala Tyr Gln Val
 1               5                  10                  15

Ser Leu Asn Ser Gly Tyr His Tyr Cys
            20                  25

<210> SEQ ID NO 18
<211> LENGTH: 25
<212> TYPE: PRT
<213> ORGANISM: Atlantic cod

<400> SEQUENCE: 18

Ile Val Gly Gly Tyr Glu Cys Thr Lys His Ser Gln Ala His Gln Val
 1               5                  10                  15

Ser Leu Asn Ser Gly Tyr His Tyr Cys
            20                  25

<210> SEQ ID NO 19
<211> LENGTH: 25
<212> TYPE: PRT
<213> ORGANISM: Atlantic cod
```

-continued

```
<400> SEQUENCE: 19

Ile Val Gly Gly Tyr Glu Cys Thr Arg His Ser Gln Ala His Gln Val
1               5                  10                  15

Ser Leu Asn Ser Gly Tyr His Tyr Cys
            20                  25

<210> SEQ ID NO 20
<211> LENGTH: 25
<212> TYPE: PRT
<213> ORGANISM: Euphasia superba
<220> FEATURE:
<221> NAME/KEY: VARIANT
<222> LOCATION: (1)...(25)
<223> OTHER INFORMATION: Xaa = Any Amino Acid

<400> SEQUENCE: 20

Ile Val Gly Gly Xaa Glu Val Thr Pro His Ala Tyr Pro Trp Gln Val
1               5                  10                  15

Gly Leu Phe Ile Asp Asp Met Tyr Phe
            20                  25
```

REMOVING DENTAL PLAQUE WITH KRILL ENZYMES

This application is a continuation of U.S. patent application Ser. No. 09/549,642, filed Apr. 14, 2000, now abandoned; which, in turn, is a divisional of U.S. patent application Ser. No. 09/303,375, filed on Apr. 30, 1999, now abandoned; which, in turn, is a divisional of U.S. patent application Ser. No. 08/600,273, filed on Feb. 8, 1996, now U.S. Pat. No. 5,958,406; which, in turn, is a continuation-in-part of U.S. patent application Ser. No. 08/486,820, filed Jun. 7, 1995, now U.S. Pat. No. 6,030,612; which, in turn, is a continuation-in-part of U.S. patent application Ser. No. 08/385,540, filed Feb. 8, 1995, now U.S. Pat. No. 5,945,102; which, in turn, is a continuation-in-part of U.S. patent application Ser. No. 08/338,501, filed on Nov. 22, 1994, now abandoned which, in turn, is a 371 national stage application of International Application no. PCT/SE93/00455, filed on May 21, 1993, designating the United States of America, under 35 U.S.C. §365(c).

The present invention relates to a krill-derived multifunctional enzyme and a family of crustacean and fish derived enzymes having substantial structural similarity to the multifunctional enzyme derived from antarctic krill. The invention additionally relates to the multifunctional enzyme, to methods of purifying the multifunctional enzyme and purified multifunctional enzyme, and to pharmaceutical, cosmetic and other uses of the enzyme.

The enzymes that are substantially structurally similar to the krill-derived multifunctional enzyme have the same utility as the krill enzyme. In particular, these multifunctional enzymes are useful for treating viral infections such as herpes outbreaks, fungal, bacterial or parasitic infections, including the primary and secondary infections of leprosy, colitis, ulcers, hemorrhoids, corneal scarring, dental plaque, acne, cystic fibrosis, blood clots, wounds, immune disorders including autoimmune disease, such as lupus erythematosus and multiple sclerosis, and cancer. The entire disclosures of U.S. patent application Ser. Nos. 08/486,820, 08/338,501 (filed Nov. 22, 1994) and Ser. No. 08/385,540 are incorporated herein by reference.

U.S. Pat. Nos. 4,801,451 and 4,963,491 disclose a mixture of exo- and endopeptidases isolated from antarctic krill (*Euphasia superba*) and the use of the mixture as cleaning solutions. U.S. Pat. No. 4,801,451 discloses the use of such enzymes to remove foreign matter and dead tissue from wounds. Patent Application WO 85/04809 discloses the use of krill enzymes as a digestion promoter. European Application EP-A1-0170115 discloses the use of krill enzymes to dissolve blood clots. All of these references employ impure or poorly characterized materials. A purified multifunctional enzyme is desirable to provide a pharmaceutically useful product.

SUMMARY OF THE INVENTION

The present invention provides a multifunctional enzyme that has been found to be useful in numerous medical and cosmetic contexts. In particular, the invention relates to an enzyme having multifunctional activity comprising at least one of a chymotrypsin; trypsin, collagenase, elastase or exo peptidase activity, a molecular weight between about 20 kd and about 40 kd as determined by SDS PAGE, and substantial homology to krill-derived multifunctional hydrolase. Preferably, the enzyme has a molecular weight of from about 26 kd to about 32 kd as determined by SDS (sodium dodecyl sulfate) polyacrylamide gel electrophoresis ("PAGE"), more preferably about 29 kd. Preferably, the enzyme is selectively reactive with cell-surface receptors such as proteins or glycolipids. Preferably, the enzyme is substantially purified. Preferably the enzyme has a purity with respect to macromolecules of at least about 90%, more preferably least about 95%, more preferably about 97%, still more preferably about 99%, yet more preferably 99.7% with respect to macromolecules. Preferably, the enzyme has an N-terminal sequence comprising: I-V-G-G-X-E/D-B-X-X-X-X-Z/B'-P-Z/H-Q-B-X-B'/Z, wherein X is any amino acid, Z is an aromatic amino acid, B is an amino acid having a C1 to C6 alkyl side chain, and B' is leucine or isoleucine. More preferably, all amino acids represented by X, Z or B are natural amino acids. Preferably, the enzyme has an N-terminal sequence comprising: I-V-G-G-X-E/D-B wherein X is any amino acid, B is an amino acid having a C1 to C6 alkyl side chain. Preferably, the enzyme is the hill-derived multifunctional hydrolase. Preferably, the enzyme has the N-terminal sequence: I-V-G-G-N/M-E-V-T-P-H-A-Y-P-W-Q-V-G-L-F-I-D-D-M-Y-F (SEQ ID NO. 1). For the purposes of this application, "substantially pure" shall mean about 60% purity.

In another preferred embodiment, the multifunctional enzyme shall have at least about 70% homology with the krill derived multifunctional hydrolase, more preferably at least about 80% homology, still more preferably at least about 90% homology, yet still more preferably at least about 95% homology. Homology measurements will score conservative substitutions as homologous. The krill-derived multifunctional hydrolase can be the multifunctional enzyme. The krill-derived multifunctional hydrolase is 100% homologous with itself.

The invention also provides a pharmaceutical composition comprising the multifunctional enzyme of claim 1 and a pharmaceutically acceptable diluent or carrier.

The invention further provides (a) methods relating to certain conditions using effective amounts of the enzyme described above, (b) compositions for use in such methods, (c) pharmaceutical compositions containing effective amounts of enzyme for use in such methods, and (d) uses of the enzyme composition for manufacturing a medicament for use in such methods. The methods are for:

(1) treating or prophylactically preventing a microbial infection [e.g. viral such as: a herpes (e.g. HSV-1, HSV-2, herpes zoster or genital herpes infection), HIV, hepatitis, influenza coronavirus, cytomegalovirus, rhinovirus or papilloma virus infection; an infection causing a gastrointestinal disease such as ulcer or diarrhoea; a fungal infection such as a systemic, skin, oral, vaginal or esophageal fungal, including, for example, yeast infection, including a fungal nail infection and candida infections; microbial infections of the eye, preferably treated with ocular administrations; bacterial infections including *staphylococcus, streptococcus, klebsiella, pseudomonas, gonorrhea, haemophilus, chlamydia, syphilis* and *E. coli* infections and bacterial infections causing chancroid; opportunistic microbial infections in immunocompromised patients where preferably the administered amount of the multifunctional enzyme, described below, is a microbial infection treating or preventing effective amount or has inhibitory activity against cell-cell or cell-virus adhesion;

(2) treating or prophylactically preventing dermatological conditions, such as, for example, acne, psoriasis or eczema, including facial seborrheic eczema or eczema of the hands, face or neck, hemorrhoids and the like, where preferably the amount of the multifunctional enzyme administered is a dermatological condition treating or preventing effective amount;

(3) treating or prophylactically preventing cystic fibrosis, COPD, cancer, for example, by administering a tumor treating effective amount or a tumor metastasis preventing or inhibiting amount of enzyme, atherosclerosis, asthma, septic shock, toxic shock syndrome, tissue adhesions such as tendon-sheath, abdominal post-surgical or joint adhesions, reperfusion injury, malaria, immune disorder such as an autoimmune disease, apoptosis, colitis and enteritis, such as Crohn's disease, where preferably the amount of the multifunctional enzyme administered is effective for treating or preventing;

(4) treating or prophylactically preventing wound infection (by applying to the wound a microbial infection preventing effective amount of the enzyme or by enhancing the healing of the wound by administering a microbe inhibiting effective amount of the enzyme), when treated the wound can be substantially free of necrotic tissue;

(5) treating or prophylactically preventing acute or chronic inflammation, where preferably the amount of the multifunctional enzyme administered is an acute or chronic inflammation treating or preventing effective amount;

(6) treating or prophylactically preventing an indication selected from the group consisting of pain, bronchitis, *haemophilus influenzae* infections, mycoplasma in lungs, foreskin infections, athlete's foot, fistulae infections, infected topical ulcers, gastric ulcers, navel infections in newborns, wrinkles, polyps, scars and keloids, lichen planus, boils, warts and allergic itch, prostatitis, mastitis, gingivitis, sinusitis, arthritis and inflamed joints, diarrhoea, eye disease, such as glaucoma or cataracts, and hair-thinness, where preferably the amount of the multifunctional enzyme administered is a treating or preventing effective amount;

(7) removing dead or peeling skin from otherwise healthy skin to improve the skin's appearance, where preferably the amount of the multifunctional enzyme administered is a dead skin removing effective amount;

(8) lysing blood clots, where preferably the amount of the multifunctional enzyme administered is a clot lysing effective amount; and (9) removing dental plaque, where preferably the amount of the multifunctional enzyme administered is a dental plaque removing effective amount.

The method comprises administering a composition comprising a the multifunctional enzyme described above. The composition of the invention can also be used to remove dead of divergent cells.

The invention provides topical cosmetic composition comprising the multifunctional enzyme described above; and cream, gel or suppository composition.

The invention also provides method of purifying the multifunctional enzyme described above to obtain a composition containing substantially no other proteins that bind a selected protease inhibitor other than the multifunctional enzyme, the method comprising the steps of:

(a) applying a composition containing the multifunctional enzyme to an ion exchange column;

(b) eluting a first adsorbed material from the column with a first aqueous solution of first ionic strength $I_1$; and (c) eluting the multifunctional enzyme from the column with a second aqueous solution of second ionic strength $I_2$;

(d) applying the eluted multifunctional enzyme from step (c) to an affinity matrix comprising the protease inhibitor; and (e) eluting the affinity matrix with a third aqueous solution that destabilizes the interaction between the multifunctional enzyme and the protease inhibitor wherein $I_1$ is selected so that the first aqueous solution (i) elutes the first adsorbed material containing proteins that can bind to the protease inhibitor, but which proteins adhere to the anion exchange column more weakly than the multifunctional enzyme and, (ii) does not elute the multifunctional enzyme; and wherein $I_2$ is greater than $I_1$ and is selected so that the second aqueous solution elutes the multifunctional enzyme and substantially no other proteins that bind the selected protease inhibitor. Preferably, the selected protease inhibitor used in the affinity matrix is resistant to digestion by the multifunctional enzyme, such as is a mammalian trypsin inhibitor, for example, bovine trypsin inhibitor.

The invention further provides (a) methods relating to certain conditions using effective amounts of the enzyme described above, (b) compositions or substances for use in such methods, (c) pharmaceutical compositions containing effective amounts of enzyme for use in such methods, and (d) uses of the enzyme for manufacturing a medicament for use in such methods. The methods are for:

(10) prophylactically preventing sexually transmitted microbial infection, such as candida such as an oral or vaginal candida infection, *gonorrhea, chlamydia, syphilis, trichomonas*, chancroid, HIV, herpes, papilloma or hepatitis infections, where the administering of enzyme described below occurs before, in conjunction with, or after sexual activity, preferably in an infection preventing effective amount;

(11) prophylactically preventing a cold or influenza virus infection, where the enzyme is preferably administered to the lungs, nasal passages or sinuses on an animal at risk of infection in a microbial infection preventing effective amount;

(12) treating or prophylactically preventing a primary or secondary microbial infection in a patient having leprosy, preferably administering in a primary or secondary infection treating or preventing effective amount;

(13) treating a tissue, body fluid or composition of cells to remove or inactivate a cell adhesion component comprising, wherein the enzyme is administered to the tissue, body fluid or composition of cells, preferably a cell-adhesion component removing or inactivating effective amount or an immune rejection inhibiting amount of the enzyme is administered, preferably the tissue, body fluid or composition of cells is treated extracorporally, although they may also be treated in situ in an animal;

(14) cleaning a contact lens, preferably applying to the lens a lens cleaning effective amount of the enzyme, where the application can be done while the lens is in the eye;

(15) treating or prophylactically preventing coronavirus, such as the coronavirus causing feline infectious peritonitis, cytomegalovirus, rhinovirus or papilloma virus (such as human papilloma virus) infection, where preferably a viral infection treating or preventing effective amount of enzyme is administered;

(16) treating or prophylactically preventing HIV infection, preferably administering an HIV infection treating or preventing effective amount of the enzyme;

(17) treating or prophylactically preventing an oral or esophageal fungal, including yeast infection, preferably by administering a microbial infection treating or preventing effective amount of the enzyme;

(18) treating or prophylactically preventing a pseudomonas, lichen planus, candida, such as a vaginal or oral candida infection, *gonorrhea, chlamydia, syphilis, trichomonas*, or chancroid infection, preferably by administering a microbial infection treating or preventing effective amount of the enzyme;

(19) prophylactically preventing, diminishing or removing a corneal scar, preferably by administering a corneal scar preventing, diminishing or removing effective amount of the enzyme, preferably the enzyme is administered in conjunction with ocular surgery to prevent the formation of a corneal scar;

(20) treating or prophylactically preventing conjunctivitis, such as viral, bacterial or allergic conjunctivitis, preferably by administering a conjunctivitis treating or preventing effective amount of the enzyme;

(21) treating or prophylactically preventing a disease or cellular process selected from the group consisting of cystic fibrosis, COPD, atherosclerosis, asthma, toxic shock syndrome, reperfusion injury, colitis, enteritis and malaria-infection associated pain, preferably by administering a treating or preventing effective amount of the enzyme;

(22) prophylactically preventing or limiting reperfusion injury, preferably by administering a reperfusion injury preventing or limiting effective amount of the enzyme;

(23) treating or prophylactically preventing the process of apoptosis in cells at risk for apoptosis, such as T-cells in HIV patients, preferably by administering an apoptosis treating or preventing effective amount of the enzyme;

(24) treating or prophylactically preventing an autoimmune disease such as multiple sclerosis, rheumatoid arthritis, lupus erythematosus, vasculitis, temporal arteritis, primary biliary cirrhosis, active chronic hepatitis, ulcerative colitis or scleroderma, preferably by administering an autoimmune disease treating or preventing effective amount of the enzyme; and

(25) treating hemorrhoids (for example, post-partum hemorrhoids) preferably by administering a hemorrhoids treating effective amount of the enzyme.

The method comprises administering a composition comprising a multifunctional enzyme described above.

The invention further provides (a) methods for treating or prophylactically preventing a cell-cell or cell-virus adhesion syndrome comprising administering an anti-adhesion effective amount of a hydrolase effective to remove or inactivate a cellular or viral acceptor or receptor adhesion component that is involved in the cell-cell or cell-virus adhesion, (b) compositions or substances for use in such methods, (c) pharmaceutical compositions containing effective amounts of enzyme for use in such methods, and (d) uses of the enzyme composition for manufacturing a medicament for use in such methods. Preferably, the syndrome comprises inflammation, shock, tumor metastases, autoimmune disease, transplantation rejection reactions or microbial infections. Preferably, (a) the syndrome is selected from the group consisting of microbial infection, immune disorder, cystic fibrosis, COPD, atherosclerosis, cancer, asthma, septic shock, toxic shock syndrome, conjunctivitis, reperfusion injury and pain, and (b) a cell surface receptor, associated with the cell-cell or cell-virus adhesion syndrome, selected from the group consisting of ICAM-1, ICAM-2, VCAM-1, CD4, CD8, CD11, CD18, CD28, CD29D, CD31, CD44, CD 49, CD62L, CD102 and asialo GM1 ceramide is removed or inactivated by the administered hydrolase. Preferably, a microbial infection is treated or prevented and the microbial infection is a herpes, HIV, hepatitis or papilloma infection; an infection causing colitis, ulcer or diarrhoea; a candida infection, such as an oral, vaginal or esophageal candida infection; a cold or influenza infection; a *pseudomonas, haemophilus, staphylococcus, streptococcus, klebsiella* or *E. coli* infection; a primary or secondary infection of leprosy; or an infection causing conjunctivitis.

The invention further provides (a) methods treating or prophylactically preventing an infection by a drug-resistant microbe by administering a treating or preventing effective amount of the multifunctional enzyme described above, (b) compositions or substances for use in such methods, (c) pharmaceutical compositions containing effective amounts of enzyme for use in such methods, and (d) uses of the enzyme composition for manufacturing a medicament for use in such methods. Preferably, the microbe is a methicillin or quinolone-resistant bacteria. In another preferred embodiment, the microbe is a fungus, such as a fungus (e.g., a candida fungus) that is resistant to azole-type drugs such as fluconazole.

The invention further provides a pharmaceutical composition for removing or inactivating a cell-surface adhesion molecule comprising a cell-surface adhesion molecule removing or inactivating effective amount of a multifunctional enzyme having: activity comprising at least one of a chymotrypsin, trypsin, collagenase, elastase or exo peptidase activity; a molecular weight between about 20 kd and about 40 kd as determined by SDS PAGE; and substantial homology to the krill-derived multifunctional hydrolase, and a pharmaceutically acceptable diluent or carrier.

The invention still further provides a pharmaceutical composition for treating or prophylactically preventing a cell-cell or cell-virus adhesion syndrome comprising a cell-cell or cell-virus adhesion syndrome treating or preventing effective amount of a composition comprising a multifunctional enzyme having: activity comprising at least one of a chymotrypsin, trypsin, collagenase, elastase or exo peptidase activity; a molecular weight between about 20 kd and about 40 kd as determined by SDS PAGE; and substantial homology to the krill-derived multifunctional hydrolase, and a pharmaceutically acceptable diluent or carrier.

Preferably, the multifunctional enzyme of the invention has at least two of the identified proteolytic activities, more preferably at least three, still more preferably at least four. Yet more preferably, the enzyme has all of the identified proteolytic activities. Preferably, the multifunctional enzyme has substantial anti cell-cell and cell-virus adhesion activity. Preferably, the multifunctional enzyme has substantial homology with the krill-derived multifunctional hydrolase.

In a preferred embodiment, HIV-infected patients are treated to slow the progression of the associated diseases by the process of (1) isolating T-cells from the patient, (2) treating the T-cells with a hydrolase effective to remove CD4, and (3) injecting the T-cells into the patient.

The method of treating tumors can be done by administering orally or parenterally, including but not limited to intravenously, intra-arterially, intraperitoneally, subcutaneously, intramuscularly or intra-tumorally. As a part of this embodiment, the invention provides a method of preventing or limiting tumor metastatic processes.

In one embodiment, the invention provides a method of inhibiting or prophylactically preventing the transmission of a pathogenic microbe by administering the multifunctional enzyme. Preferably, the multifunctional enzyme is applied to the portion of the body that comprises the primary transmission entryway for the microbe in question. In one preferred embodiment, a spray, ointment or wash is applied to a body orifice involved in sexual activity, for instance, to prevent HIV or hepatitis transmission. In another preferred embodiment, the multifunctional enzyme is applied to the upper airways, for example, via an aerosol, to inhibit or prevent the transmission of a cold virus, such as a rhinovirus or a corona virus.

In one aspect, the method of extra-corporeally treating a tissue, body fluid or composition of cells to remove cell adhesion components reduces the immune rejection of a tissue, body fluid or composition of cells that is transplanted from one individual to another. In another aspect, such treatments remove or inactivate the cell adhesion components found in the treated tissue, body fluid or composition of cells involved a microbial infection.

In treating or prophylactically preventing septic shock or toxic shock syndrome by administering the multifunctional enzyme, appropriate routes of administration would include without limitation systemic administration. For vaginal infections associated with shock, vaginal flushes, creams, gels or suppositories will preferably also be used as a method of administration.

The invention further relates to a method of prophylactically preventing sexually transmitted disease by applying a microbial infection preventing effective amount of the multifunctional enzyme to a birth control device. Further, the invention provides birth control devices comprising the multifunctional enzyme.

In inhibiting or preventing the process of apoptosis, or programmed cell death, the enzyme can be administered in vivo or ex vivo.

In a preferred embodiment of the invention, the multifunctional enzyme is isolated in a form that is essentially free of any trypsin inhibitor. By "essentially free", it is meant that no such trypsin inhibitor is detectable by Coomassie Blue staining when 15 μg of isolated multifunctional enzyme is analyzed by SDS-PAGE. Preferably, no trypsin inhibitor is detectable by silver staining when 1 μg isolated multifunctional enzyme is analyzed by SDS-PAGE.

BRIEF DESCRIPTION OF THE DRAWINGS

FIG. 11 shows the pain relief experienced by lame race horses treated with the poly-enzyme preparation of Example 1A.

FIG. 12 shows certain indicators of healing following the treatment necrotic wounds with the multifunctional enzyme purified as described in Example 1B.

DETAILED DESCRIPTION

Figure 1A:
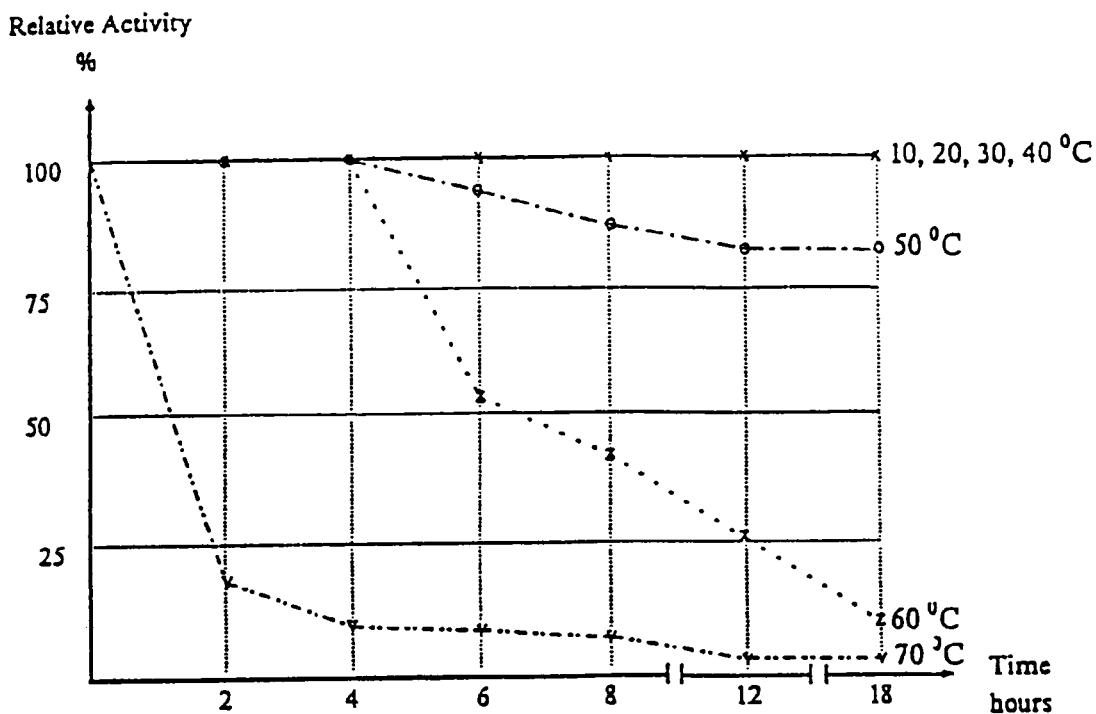
FIGS. 1A and 1B show the temperature stability of the poly-enzyme preparation of Example 1A when incubated at various temperatures over time scales of hours or days.
Figure 1B:
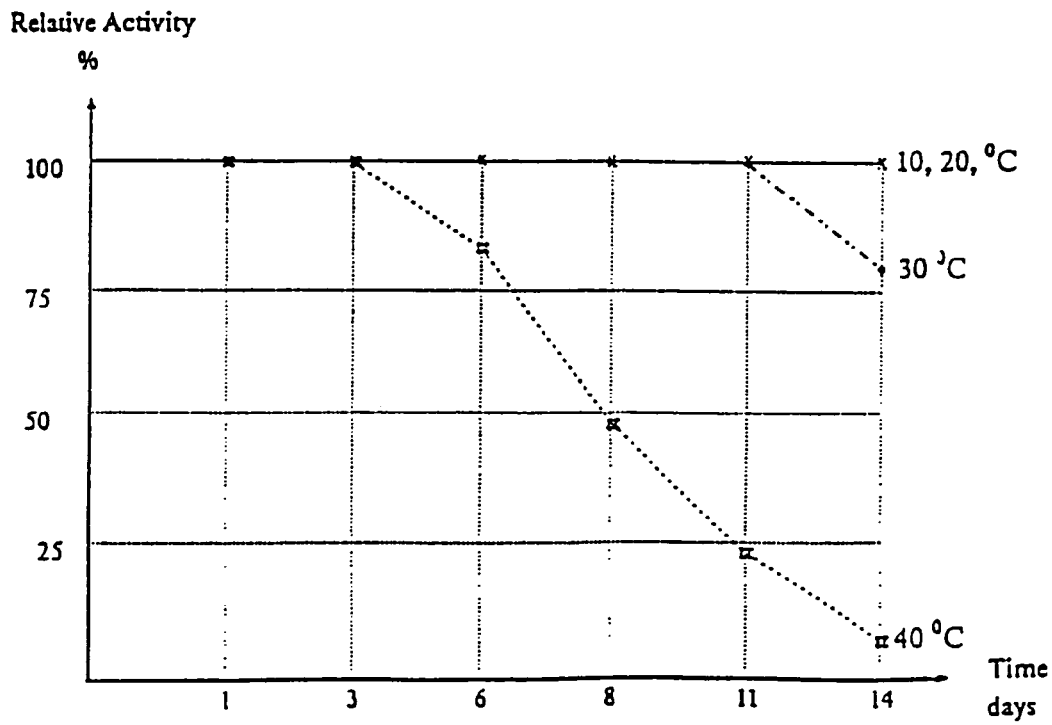

It has now been established that the multifunctional enzyme of the invention effectively removes or inactivates certain cell-surface adhesion molecules, such as ICAM-1 (i.e., CD 54), ICAM-2, VCAM-1, CD4, CD8, CD28, CD31, CD44 and the asialo GM1 ceramide, without affecting cell viability. This adhesion site removal or inactivation phenomenon is believed to provide at least a partial explanation for the enzyme's effectiveness against many, though probably not all, of the indications against which the multifunctional enzyme is effective. Other cell surface receptors have been found to be substantially resistant to removal or inactivation by the multifunctional protein, such as the T-cell receptor, the Class I major histocompatibility complex or the integrins CD11 and CD18.

While not wishing to be restricted by any particular theory, it is believed that the activity of the multifunctional enzyme in preventing or treating infections by cold viruses relates to the enzyme's anti-adhesion activity. For instance, rhinoviruses, which are responsible for the majority of colds, infect by a pathway that utilizes an interaction between virus and ICAM-1 cell-surface adhesion molecule. See Lineberger at al., *J. Virol.* 64:2582-2587 (1990); Stauton et al., *Cell* 61:243-254 (1990). The multifunctional enzyme removes or inactivates ICAM-1 from mammalian cell surfaces. Analogously, the infective pathway for coronaviruses, which are responsible for most colds not caused by a rhinovirus, utilizes the CD13 cell-surface molecule. See Delman et al., *Nature,* 357: 417-420 (1992); Yeager et al., *Nature,* 357:420-422 (1992). It is believed that multifunctional enzyme removes or inactivates a cell surface adhesion molecule involved in the infective pathway for coronaviruses. Because of the multifunctional enzyme's stability and the broad pH range over which it is effective, the enzyme can function in a number of environments, such as the lungs, sinuses, mouth, intestines and vagina, where it can be applied.

While not wishing to be restricted by any particular theory, the pain-relieving activity of the multifunctional enzyme in malaria is believed to be due at least in part to the enzyme's activity against the ICAM-1 cell-surface adhesion molecule. ICAM-1 is involved in adhering infected red blood cells (RBCs) to the endothelium and to uninfected RBCs, causing obstructions in the patient's capillaries and venules and the pain associated with the crises of malarial infections. Ockenhouse, "Cell Adhesion Molecules in Host Parasite Interactors" in *Adhesion Molecules*, Craig Wegner, Ed., Academic Press, San Diego, 1994, pp. 277-291. The multifunctional enzyme removes or inactivates ICAM-1 from cell surfaces.

A number of cell-surface adhesion molecules are involved in reperfusion injury, including the ICAM-1 molecule. Korthius and Granger, "Pathogenesis of Ischemial/Reperfusion," in *Adhesion Molecules*, Wegner, Ed., Academic Press, 1994, pp. 163-190. ICAM-1 specific antibodies interfere with neutrophil adherence to and migration into ischemic tissue, Id., thereby limiting the role of neutrophils in re-perfusion injury. These antibodies can also limit the size of a myocardial infarction. Id. at 177, FIG. 8.17. The multifunctional enzyme interferes with ICAM-1 by removing it from the cell surface or by inactivating it.

Again not wishing to be limited by any particular theory, the anti-CD4 cell surface adhesion molecule activity of the multifunctional enzyme is believed to be responsible, at least in part, for the enzyme's HIV-transmission inhibitory activity. The HIV infective pathway utilizes the CD4 cell-surface molecule. See, Lentz, "Molecular Interaction of Viruses with Host-Cell Receptors," in *Adhesion Molecules*, Wegner, Ed., Academic Press, 1994, pp. 223-251 at p. 229.

In *candida* infections, the hyphal stage is believed to be more infective. Ligands on the *candida* fungi that possibly recognize a GalNAcβ(1-4)Gal carbohydrate structure on asialo-GM1 ceramides of the infection host, are believed to be involved in the process by which candida infect. Such ligand molecules may also be involved in the process by which candida yeast are converted to the hypal stage. In *pseudomonas* infections of the lungs, a bacterial cell-surface ligand that recognizes a GalNAcβ(1-4)Gal carbohydrate structure is believed to play a role in the lung infection pathway. Abraham, "Bacterial Adhesions," in *Adhesion Molecules*, Wegner, Ed., Academic Press, 1994, pp. 253-276. The same or similar glycolipid structure is believed to be involved in adhering several pathogens to the lungs, including *Pseudomonas aeruginosa, Haemophilus influenzae, Staphylococcus aureus, Streptococcus pneumoniae, Klebsiella pneumoniae* and certain isolates of *E. coli*. See, Krivan et al., *Proc. Natl. Acad. Sci. U.S.A.* 85: 6157-6161, 1988.

Wrinkled skin to a major part is caused by free radicals crosslinking collagen. The formation of free radicals is believed to be caused by the interplay between dead or dying cells and bacteria, which find such cells to provide an excellent growth medium. While not wishing to be bound to a particular theory, it is believed that the anti-adhesion properties of the multifunctional enzyme decrease the adherence to skin of the bacteria involved in free radical formation.

Bacteria flourishing on dead, dying or divergent cells are believed to produce toxins that play a role in hair thinning. The toxins trigger skin cells to produce factors such as tumor necrosis factor, which in turn affect hair growth negatively. While not wishing to be bound to a particular theory, it is believed that the anti-adhesion properties of the multifunctional enzyme helps to stabilize or reverse the hair thinning process.

CD4 and ICAM-1 are believed to be involved in T-cell apoptosis. See, Okazaki et al., *Cell. Immunol.* 156: 135-45 (1994). Again not wishing to be limited to a particular theory, it is believed that the anti-adhesion properties of the multifunctional enzyme play a role in inhibiting apoptosis.

Gastric ulcer is a disease that is often associated with bacterial infection with *helicobacter pylori*. While not wishing to be limited to a particular theory, it is believed that the multifunctional enzyme of the invention acts on ulcers by inhibiting bacterial attachment to the gastro-intestinal mucosa.

Studies on the destruction or inactivation of cell surface molecules on T-cell exposed to as little as 10 μg/ml of the krill hydrolase for four hours at 37° C. have determined that: CD3 and CD90 are largely unaffected; CD28, CD49, CD29D, CD18 and CD11 are significantly destroyed or inactivated, about 25% to about 40% reduction detectable antigen; CD54, CD102, CD44, CD31, CD62L, CD4, and CD8 are substantially destroyed or inactivated, generally about 70% to about 100% reduction in detectable antigen. Additionally, antibodies against asialo GM-1 have indicated reductions in the immunologically detectable amount of this ceramide in the membranes of lung epithelial cells following exposure to the multifunctional enzyme of the invention. Further, such treatment of lung epithelial cells reduces the level attachment of *Pseudomonas* bacteria to the lung epithelial cells.

It is believed that the above discussed adhesion molecules and others will prove to play a role in a number of other diseases for which the multifunctional enzyme is an effective treatment or preventative agent.

For the purposes of this application, the terms listed below shall have the following meaning:

at risk of infection
    an animal is at risk of infection if some feature of its environment or medical history is correlated with an increased risk of one or more infections.

cell-cell or cell-virus adhesion syndrome
    a disease in which a receptor or acceptor cell adhesion component plays a role in the etiology of the disease, for instance by playing a role in the development, transmission, growth or course of the disease.

cell adhesion component involved in a microbial infection
    a cell adhesion component used by a microbe to facilitate adherence to a tissue or cell at risk of infection.

dermatological condition
    a condition relating to lesions of the topical surface of an animal, including without limitation the skin, the vagina and the surface of the eyes.

derived from fish or crustacean
    refers to an enzyme having the same sequence as an enzyme isolated from fish or crustacean.

drug-resistant
    a microbe of a type that is or once was generally sensitive to given amounts of one or more antimicrobial agents but which is not sensitive to the agents or is only sensitive at significantly higher amounts.

hydrolase
    an enzyme that degrades bonds formed by dehydration reactions such as amide, ester, or ether bonds, The term encompasses, but is not limited to, proteases such as trypsin and chymotrypsin.

immune disorder
    any disorder caused by an immune reaction to foreign substances, tissues or cells or to autologous or transplanted tissue. The term encompasses autoimmune diseases.

krill-derived multifunctional hydrolase
    a multifunctional enzyme having the same sequence as the enzyme isolated from krill having the properties of the protein described in Examples 1B, 1C and 1D. This enzyme is also referred to as the "krill multifunctional hydrolase" or the "krill multifunctional enzyme" or the "krill-derived multifunctional enzyme."

macromolecule
    for determining purity, this means a biological polymer such as a protein, nucleic acid or carbohydrate of molecular weight greater than about 1000.

microbes
    bacteria, mycoplasma, yeasts, fungi, virus, protozoa, parasites (such as malaria parasites) and the like.

multifunctional enzyme
    an enzyme having activity comprising at least one of a chymotrypsin, trypsin, collagenase, elastase or exo peptidase activity, a molecular weight between about 20 kd and about 40 kd, and substantial homology to krill-derived multifunctional hydrolase.

necrotic tissue
    a portion of tissue made up of dead or irreversibly damaged cells.

protein
: for the purpose of determining purity, this means a polypeptide of molecular weight greater than about 1000.

reactive with a cell-surface protein or glycolipid
: means removes, destroys, inactivates or disables the detectable presence of the cell-surface molecule, by whatever mechanism.

reactive with a cellular or viral acceptor or receptor adhesion component
: means removes, destroys, inactivates or disables a cell's or a virus' ability to interact with a cell, virus, ligand, group or molecule, regardless of the mechanism.

SDS-PAGE
: means polyacrylamide gel electrophoresis of proteins in the presence of sodium dodecyl sulfate.

selectively reactive with a cell-surface protein
: means removes, destroys, inactivates or disables certain cell-surface proteins on the surface of a cell but not others.

sexually transmitted microbial infection
: any microbial disease that is transmitted during sexual contact.

substantial homology
: at least about 60% sequence homology.

substantially no other proteins that bind a selected protease inhibitor
: a composition contains substantially no other proteins that bind a selected protease inhibitor if such proteins comprise no more than about 5% w/w of the total protein in the composition.

systemic administration
: an administration of a biological agent, such as the multifunctional enzyme, designed deliver the agent to the blood or other circulatory system (such as the lymphatic system) of an animal.

Crustaceans, including antarctic krill, are useful sources for the multifunctional enzyme of the invention. For instance, frozen krill can be homogenized in water or buffer, preferably containing an antimicrobial agent. The supernate, diluted if appropriate, can then be fractionated by ion exchange chromatography (preferably anion exchange chromatography), gel filtration, chromatofocusing chromatography, or other traditional separation process. Preferably, however, some part of the separation process will include affinity chromatography using a matrix having attached molecules of a trypsin inhibitor, such as soybean trypsin inhibitor. The krill-derived multifunctional hydrolase used in the invention can be desorbed from such a matrix by applying conditions that will destabilize the interaction between the hydrolase and the inhibitor. Such conditions include high salt, low pH or the presence of denaturants such as urea. To add another selective process, the destabilizing condition can be applied to the matrix incrementally, as in a gradient. When affinity chromatography is used, it will preferably be followed with chromatography using a matrix having attached molecules of the multifunctional enzyme used in the invention. This enzyme affinity step serves to remove molecules of trypsin inhibitor that leach off the first affinity matrix. By these methods, multifunctional enzyme with a purity in excess of about 95%, such as a purity of about 99.7% or more, can be isolated.

The multifunctional enzyme isolated from a non-krill source can be compared to isolated krill multifunctional hydrolase for molecular weight, sequence, temperature or pH stability, temperature or pH optima and proteolytic specificity, or for other properties of the krill-derived multifunctional enzyme exemplified in the examples.

Protease activity can be determined by incubating an enzyme preparation with casein (concentration: 1% w/v) at 30° C. for 20 hours and measuring the release of amino acids or peptides (which can be measured by the increase in colorometrically determinable amino groups). Isolated multifunctional enzyme of 95% purity will typically have a specific activity of at least about 25 Casein Units per mg. Casein Units are defined in *Biochem. J.*, 173: 291-298, 1978 (using azocasein as the substrate).

Alternatively, tryptic protease activity can be measured against tyrosine-arginine-methyl-ester ("TAME"). The multifunctional enzyme (of at least about 95% purity) will preferably have specific activity of at least about 60 TAME Units per mg. Or, tryptic activity can be measured using Benzoyl-Val-Gly-Arg-p-$NO_2$-anilide as the substrate. Using this substrate and the method of *Biochemical J.*, 185: 423-433, 1980, the multifunctional enzyme will preferably have specific activity of at least about 210 Units per mg. Chymotryptic activity can be measured using Succinyl-Ala-Ala-Pro-Phe-p-$NO_2$-anilide as the substrate. Using this substrate and the method of *J. Biol. Chem.*, 269: 19565-19572, 1994, the multifunctional enzyme will preferably have specific activity at least about 260 Units per mg. Elastase activity can be measured using Boc-Ala-Ala-Pro-Ala-p-$NO_2$-anilide as the substrate. Using this substrate and the method of *J. Biol. Chem.*, 269: 19565-19572, 1994, the multifunctional enzyme will preferably have specific activity of at least about 270 Units per mg.

Protein purity is generally determined by SDS-PAGE with Coomassie blue staining. The percent staining in the appropriate band reflects the purity. Protein concentrations are generally determined by amino acid analysis or by absorbance at 280 nm.

Generally, the multifunctional enzyme will be sufficiently stabile so that at least about 50% of the proteolytic activity is retained after incubation at 50° C. for 24 hours at pH 7.0 at a concentration of 5 mg/ml. Preferably at least about 50% of the proteolytic activity is retained after incubation at 60° C. for 5 hours at pH 7.0 at a concentration of 5 mg/ml.

Preferably, the pH optimum of the multifunctional enzyme is substrate dependent. For the substrate azocasein, the pH optimum is preferably from about 3.5 to about 6.5, more preferably, from about 4.0 to about 6.0. For the substrate Benzoyl-Val-Gly-Arg-p-nitroanilide, the pH optimum is preferably in excess of about 8.0, more preferably in excess of about 9.0. For the substrate Boc-Ala-Ala-Pro-Ala-p-nitroanilide, the pH optimum is preferably between about 6.0 and about 7.0, more preferably about 7.0.

Using Benzoyl-Val-Gly-Arg-p-nitroanilide as the substrate, the $K_m$ at about pH 9.5 in the presence of 2 mM $Ca^{2+}$ is preferably between about 200 and about 240 µM. Using Succinyl-Ala-Ala-Pro-Phe-p-nitroanilide as the substrate, the $K_m$ at pH 9.5 in the presence of 2 mM $Ca^{2+}$ is preferably between about 250 and about 290 µM.

Preferably, the multifunctional enzyme has a temperature optimum for activity against casein of between about 45° C. and about 60° C. Generally, the enzyme retains at least about 50% of its activity when incubated at 5 mg/ml for 18 hours at a pH ranging from about 5.0 to about 9.5 at 25° C.

When HL60 cells are pretreated with the krill multifunctional hydrolase, their binding to TNFα stimulated endothelial cells is inhibited by more than about 60%. Preferably, treatment of HL60 or endothelial cells with the multifunctional enzyme of the invention will inhibit HL60 cell binding to TNFα stimulated endothelial cells by at least about 20%, more preferably at least about 40%, still more preferably at least about 60%, yet more preferably at least about 80%.

Alternately, the multifunctional enzyme will preferably have at least about 30% of the adhesion-inhibiting activity of the krill-derived multifunctional hydrolase. More preferably, the multifunctional enzyme shall have at least about 60% of the adhesion inhibiting activity of the krill-derived multifunctional hydrolase, still more preferably at least about 80%, yet more preferably at least about 100%.

The multifunctional enzyme of the invention is administered orally, topically, rectally, vaginally, by instillation (for instance into the urinary tract or into fistulas), by pulmonary route by use of an aerosol, by application of drops to the eye, or systemically, such as parenterally, including, for example, intramuscularly, subcutaneously, intraperitoneally, intraarterially or intravenously. The multifunctional enzyme is administered alone, or it is combined with a pharmaceutically-acceptable carrier or excipient according to standard pharmaceutical practice. For the oral mode of administration, the multifunctional enzyme is used in the form of tablets, capsules, lozenges, chewing gum, troches, powders, syrups, elixirs, aqueous solutions and suspensions, and the like. In the case of tablets, carriers that is used include lactose, sodium citrate and salts of phosphoric acid. Various disintegrants such as starch, and lubricating agents such as magnesium stearate and talc, are commonly used in tablets. For oral administration in capsule form, useful diluents are lactose and high molecular weight polyethylene glycols. If desired, certain sweetening and/or flavoring agents are added. For parenteral administration, sterile solutions of the multifunctional enzyme are usually prepared, and the pHs of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or polyvinyl alcohol, preservatives such as sorbic acid, EDTA or benzylchronium chloride, and the usual quantities of diluents and/or carriers. For pulmonary administration, diluents and/or carriers will be selected to be appropriate to allow the formation of an aerosol. For topical administrations, the multifunctional enzyme is typically administered in aqueous form or in a hydrogel. A preferred hydrogel comprises an aqueous suspension of from about 1% (w/v) to about 10% of low molecular weight hydrolyzed starch.

Suppository forms of the multifunctional enzyme are useful for vaginal, urethral and rectal administrations. Such suppositories will generally be constructed of a mixture of substances that is solid at room temperature but melts at body temperature. The substances commonly used to create such vehicles include theobroma oil, glycerinated gelatin, hydrogenated vegetable oils, mixtures of polyethylene glycols of various molecular weighty and fatty acid esters of polyethylene glycol. See, Remington's Pharmaceutical Sciences, 16th Ed., Mack Publishing, Easton, Pa., 1980, pp. 1530-1533 for further discussion of suppository dosage forms. Analogous gels or cremes can be used for vaginal, urethral and rectal administrations.

Numerous administration vehicles will be apparent to those of ordinary skill in the art, including without limitation slow release formulations, liposomal formulations and polymeric matrices.

For topical treatments, a suitable dose of multifunctional enzyme per application ranges from about 0.1 $\mu g/cm^2$ to about 1 $mg/cm^2$, preferably from about 1 $\mu g/cm^2$ (for example, using about 10 μg/ml) to about 1 $mg/cm^2$ (for example, using about 10 mg/ml), more preferably from about 5 $\mu g/cm^2$ (for example, using about 50 μg/ml) to about 100 $\mu g/cm^2$ (for example, using about 1 mg/ml), yet more preferably from about 10 $\mu g/cm^2$ to about 250 $\mu g/cm^2$, still yet more preferably from about 10 $\mu g/cm^2$ (for example, using about 100 μg/ml) to about 50 $\mu g/cm^2$ (for example, about 500 μg/ml). For systemic treatments, dosages will generally be selected to maintain a serum level of multifunctional enzyme between about 0.1 μg/100 cc and about 5 μg/100 cc, preferably between about 0.5 μg/100 cc and about 2.0 μg/100 cc. In an alternative measure of preferred systemic administration amounts, preferably from about 0.1 mg/kg to about 10 mg/kg, more preferably about 1 mg/kg, will be administered (although toxicology in animal models suggests that in excess of 25 mg/kg is acceptable). For ocular treatments, a suitable dose of multifunctional enzyme per application ranges from about 0.01 mg per eye to about 5 mg per eye, preferably from about 0.1 mg per eye to about 2.0 mg per eye. For vaginal and urinary tract treatments, suitable flushing/instillation solutions of the multifunctional enzyme will generally have concentrations from about 1 μg/ml to about 15 mg/ml, preferably from about 100 μg/ml to about 3 mg/ml. For oral treatments, suitable mouthwash solutions will generally have concentration of multifunctional enzyme from about 1 mg/ml to about 15 mg/ml preferably from about 2 mg/ml to about 10 mg/ml. Lozenges will typically contain from about 100 μg to about 10 mg of multifunctional enzyme. Aerosols will generally be made from solutions having enzyme concentrations from about 0.1 mg/ml to about 15 mg/ml, preferably from about 1 mg/ml to about 10 mg/ml. Generally, from about 0.1 ml to about 2 ml of aerosol will be applied to the airways of the patient, preferably from about 0.5 ml to about 1.0 ml. For scar and keloid treatments, generally between about 0.1 mg and about 5 mg of multifunctional enzyme will be injected into each $cm^2$ of the lesion, preferably from about 0.5 mg to about 3 mg. For treating adhered connective tissue or joints, generally between about 0.5 mg and about 10 mg of multifunctional enzyme will be injected interstitially at the adhesion, preferably between about 1 mg and about 5 mg. For all treatments, the enzyme composition will generally be applied from about 1 to about 10 times per day, preferably from about 2 to about 5 times per day. These values, of course, will vary with a number of factors including the type and severity of the disease, and the age, weight and medical condition of the patient, as will be recognized by those of ordinary skill in the medical arts. It is believed that substantially higher doses can be used without substantial adverse effect.

For treating or preventing infection, the multifunctional enzyme can be administered systemically or in a manner adapted to target the affected tissue. For preventing cold or influenza transmission, the composition is preferably applied to the lungs or airways. For treating immune disorders, the composition may, be applied systemically or in a manner adapted to target the affected tissue. For treating the primary and secondary infections of leprosy, the primary administration route will generally be the topical route. For treating scar or keloid tissue, generally the composition will be injected into the scar or keloid, except that for corneal scars the composition will generally be applied ocularly without injection. For cancer treatment, the composition will generally be administered systemically by a route or in a manner adopted to target the affected tissue. For treating atherosclerosis, the composition will generally be administered systemically, although the site of administration may be chosen to administer the highest dosages to the portion of the circulatory system most at risk. For asthma, the general route of administration will be pulmonary. For treating pseudomonas infections, the infection will typically be a lung infection and the administration route pulmonary. For reperfusion injury, the composition will generally be administered systemically, although the site of administration may be designed to administer the highest dosages to the portion of the body that suffered an ischemic event. For treating the painful symptoms of malaria, the administration mode will generally by systemic.

For wound healing, the multifunctional enzyme is preferably be applied more often than simply the time at which the wound is first dressed. Preferably, the multifunctional enzyme is applied at least about every time the wound dressing is changed. The multifunctional enzyme can also be applied at least about every other day, more preferably, every day. In one embodiment, the multifunctional enzyme is administered to a wound substantially free of necrotic tissue. The phrase "substantially free of necrotic tissue" shall mean sufficiently lacking in necrotic tissue so that an ordinarily-skilled pathologist would consider any residue of necrotic tissue to be irrelevant to determining a wound-healing prognosis.

For organ transplants, the organ to be transplanted will preferably be bathed in a solution of the multifunctional enzyme for between about 10 minutes and about 5 hours. The enzyme solution will preferably contain between about 0.01 mg/ml and about 25 mg/ml of the multifunctional enzyme, more preferably, between about 0.5 mg/ml and about 5 mg/ml. After transplantation, the multifunctional enzyme will preferably be administered systemically using the conditions described above.

For cleaning contact lenses in situ the solutions described above for ocular treatments are preferred; For ex vivo treatments, higher concentrations of enzyme will generally be used. Cleaning incubations of from about 5 to about 30 minutes at from about 20° C. to about 50° C. are also preferred. For ex vivo treatments, the higher end of the temperature range is preferred.

For leprosy, many of the associated infections will be appropriately treated with a topical application of the multifunctional enzyme. For CF or COPD, the multifunctional enzyme can be used to treat (a) the build up of viscous fluids in the lungs and (b) associated pulmonary infections. Preferably, treatments of CF and COPD patients include pulmonary treatments with an aerosol of the multifunctional enzyme, but can include other routes of administration including systemic administrations.

Particularly important among the diseases relevant to the transmission inhibitory embodiment of the invention are sexually-transmitted diseases, such as candida, *gonorrhea, chlamydia, syphilis, trichomonas*, chancroid, HIV, herpes or hepatitis infections. Among these, viral diseases are particularly preferred targets for transmission prevention; HIV is a still more preferred target. For this use, the body cavity involved in sexual activity is generally rinsed or flushed with a composition containing the multifunctional enzyme, or a creme, gel or suppository designed to localize the composition to the body cavity is used. The composition can be used soon before, in conjunction with, or soon after, sexual activity, although prior or concurrent use is preferred.

For herpes infections, the viral targets include HSV-1, which primarily manifests as oral herpes, HSV-2, which primarily manifests as genital herpes, and herpes zoster.

For autoimmune diseases or diseases with autoimmune components, treatment targets include without limitation rheumatoid arthritis, multiple sclerosis, primary biliary cirrhosis, active chronic hepatitis, ulcerative colitis, rheumatic arthritis, scleroderma, systemic lupus erythematosus, Hashimoto's thyroiditis, primary myxedema, thyroxicosis, pernicious anemia, Addison's disease, premature onset of menopause, autoimmune male infertility, insulin-dependent diabetes, type B insulin resistance of *acanthosis nigricans*, alopic allergy, myasthenia gravis, Lambert-Eaton syndrome, Goodpasture's syndrome, pemphigus vulgaris, pemphigoid, phacogenic uveitis, sympathetic ophthalmia, autoimmune hemolytic anemia, idiopathic thrombocytopenic purpura, Sjogren's syndrome, discoid lupus erythematosus, dermatomyositis and mixed connective tissue disease.

For adhesion disorders, the cells or viruses involved can include, without limitation, endothelial cells, lymphocytes, including T-cells, tumor cells, microbial cells, viruses, including HIV and herpes. Adhesion processes are believed to be involved in tissue invasion, for instance, by immune cells, microbes, and tumor cells.

As illustrated in many of the clinical examples below, the multifunctional enzyme of the invention is effective to treat or prevent inflammation. Typically, inflammations are reduced to acceptable levels within 3 or 4 days of the start of treatment. The examples also illustrate that the enzyme is effective to alleviate pain. Pain relief is often reported within 20 minutes to 2 hours of the start of treatment. Pain relief was not accompanied by loss of feeling in the treated tissue. More complete pain relief, such that the patient only suffered mild pain or a feeling of tenderness, was often experienced within 2 days of the start of treatment. While measurement of this parameter is often subjective, the examples include treatments of inflamed horse joints, for which pain relief is more objectively measured by observing the walking stride of the treated horse.

For many of diseases for which the multifunctional enzyme of the invention is useful as a prophylactic treatment, including those not caused by microbes, a patient's medical history, lifestyle or genetic background will often indicate a predisposition to acquire the disease. This is true, for instance, of atherosclerosis.

Preferred hydrolases are proteases. Particularly preferred is the multifunctional enzyme of the invention.

Generally, the multifunctional enzyme will be administered in an effective amount. An effective amount is an amount effective to either (1) reduce the symptoms of the disease sought to be treated, (2) induce a pharmacological change relevant to treating the disease sought to be treated, (3) inhibit or prevent infection or re-infection by an infective agent, or (4) prevent the occurrence of a non-infectious disease (for instance a disease treatable by blocking a cell adhesion phenomenon). For cancer, an effective amount further includes an amount effective to: prevent or limit metastasis, for instance, to reduce the level of metastasis; reduce the size of a tumor; slow the growth of a tumor; and increase the life expectancy of the affected animal. For wound treatment, in one aspect, an effective amount includes an amount which, if regularly applied, prevents the occurrence of infection. In another aspect, for wound healing, an effective amount includes an amount effective to reduce the average time it takes for a wound to heal.

Humans are the preferred subjects for treatment. However, the multifunctional enzyme can be used in many veterinary contexts to treat animals, preferably to treat mammals, as will be recognized by those of ordinary skill in light of the present disclosure.

Numerous methods for determining percent homology are known in the art. One preferred method is to use version 6.0 of the GAP computer program for making sequence comparisons. The program is available from the University of Wisconsin Genetics Computer Group and utilizes the alignment method of Needleman and Wunsch, *J. Mol. Biol.* 48, 443, 1970 as revised by Smith and Waterman, *Adv. Appl. Math.*, 2, 482, 1981. Another available method uses the FASTA computer program.

The multifunctional enzyme has been observed to treat infections. However, its direct effect on the growth of microbes in vitro is small. While not wishing to be limited by any particular theory, it is believed that the enzyme attacks the mechanisms by which microbes and tumors invade tissues. These mechanisms include cell-cell or cell-virus adhesion mechanisms by which a tumor or microbe may establish itself in a tissue. The importance of cell-surface adhesion molecules and adhesion processes in tumor metastasis is illustrated by the discussion in a Albelda, "Role of Cell Adhesion Molecules in Tumor Progression and Metastasis," in *Adhesion Molecules*, Craig Wegner, Ed., Academic Press, San Diego, 1994, pp. 71-88.

The disruption of other cell-cell or cell-virus adhesion reactions by the multifunctional enzyme is believed to be relevant to other conditions that are treatable with the multifunctional enzyme, including dental plaque and immune disorders.

The adhesion of HL60 cells (a human lymphocyte cell line) to endothelial cells is believed to model a mechanism for tumor cell invasion and infection more generally. This adhesion is stimulated by tumor necrosis factor α ("TNFα") and inhibited by antibodies to the E-selectin antigen on HL60 cells. E-selectin is a cell surface adhesion protein that appears to bind to a sialated carbohydrate. See, Bevilacqua et al., *Science* (1989) 243:1160.

Preparations of the multifunctional enzyme are active even when not purified to homogeneity. In an illustrative purification set forth below in Example 1A, a "poly-enzyme" composition containing at least six proteins was prepared. This preparation was found to be active in numerous contexts, as illustrated in many of the examples.

At least one of the enzymes present in the poly-enzyme preparation is krill multifunctional hydrolase and has at least one of chymotrypsin, trypsin, elastase, collagenase or exo peptidase activity. This hydrolase can be substantially purified by traditional methods to an apparent purity of at least about 90%. The krill-derived multifunctional hydrolase displays an apparent molecular weight of about 29 kd.

Useful preparations of the poly-enzyme preparation will generally comprise, with respect to proteins, at least about 10% of the multifunctional enzyme. Preferably preparations of poly-enzyme preparation will comprise at least 30% of the multifunctional enzyme.

Figure 2:
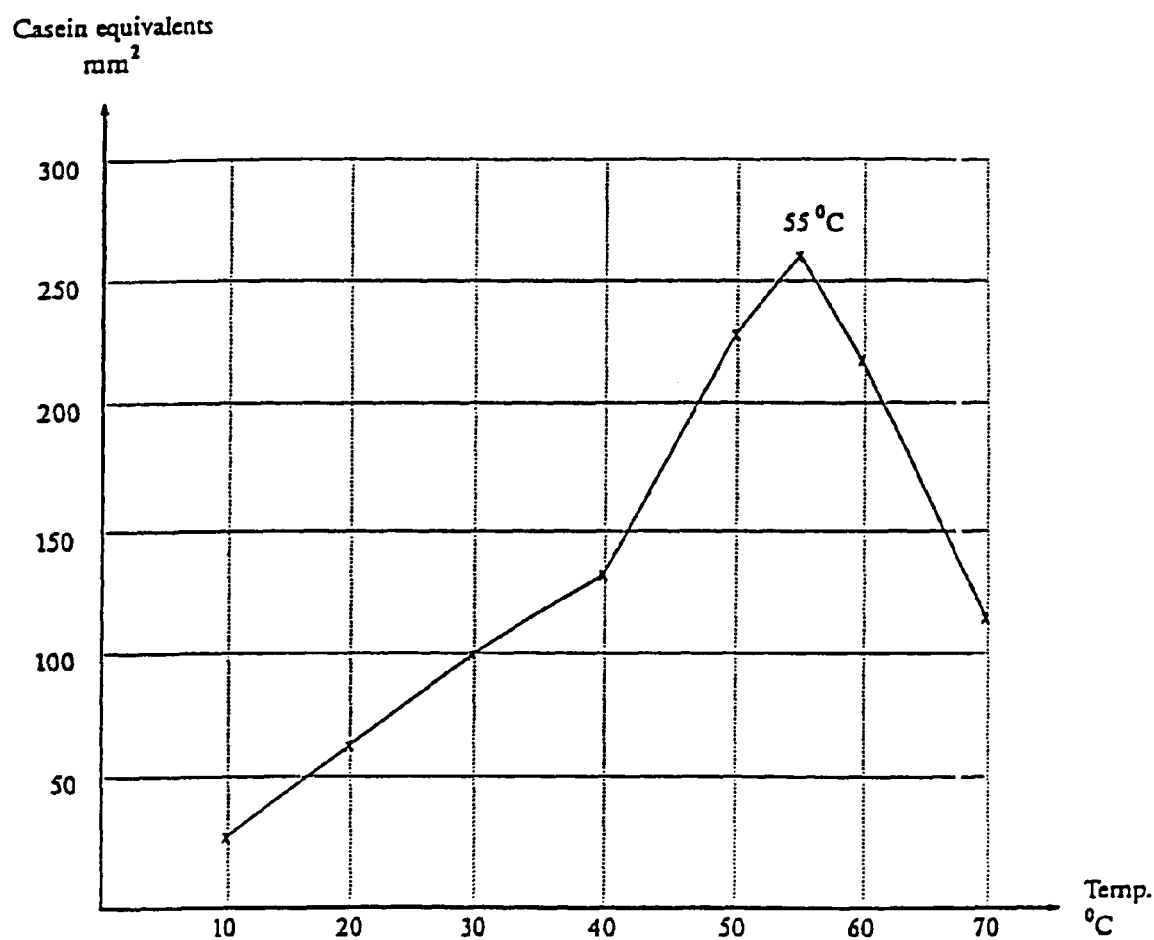
FIG. 2 shows the temperature optimum of the poly-enzyme preparation of Example 1A.
Figure 3:
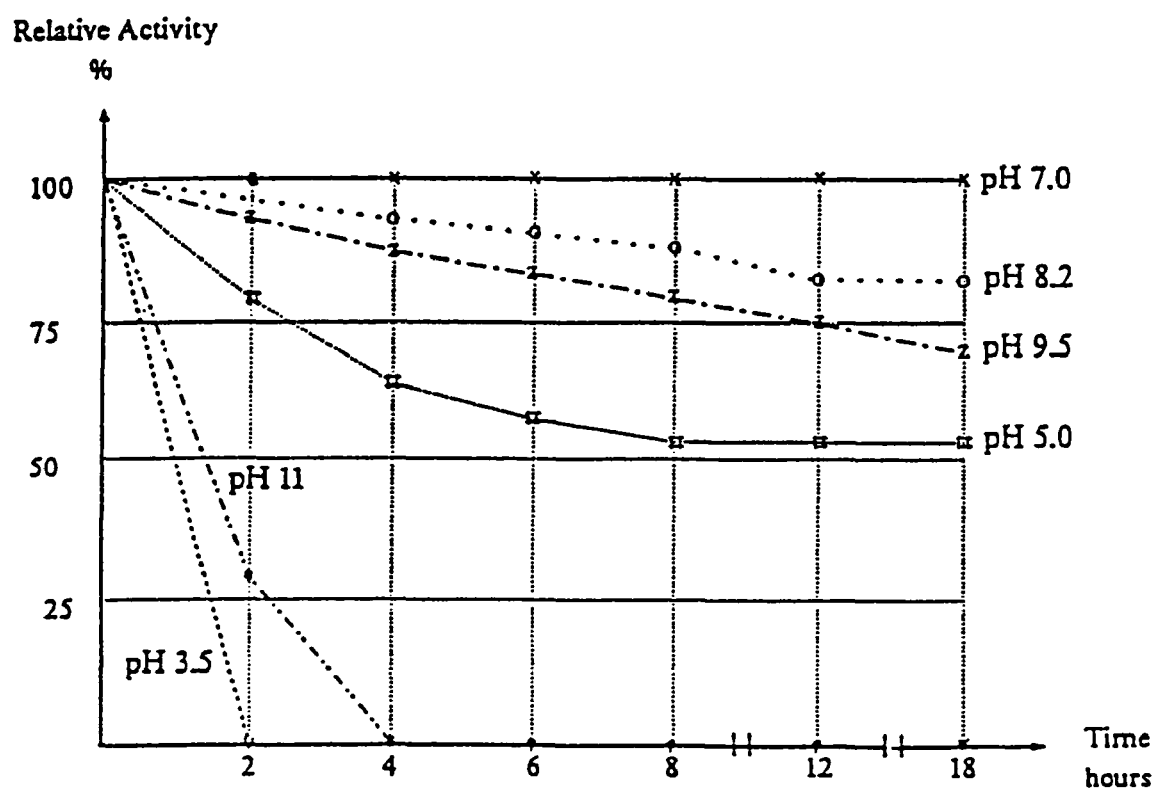
FIG. 3 shows the pH stability of the poly-enzyme preparation of Example 1A.

In FIGS. 1A and B, the temperature stability profiles the krill poly-enzyme preparation are displayed. Preparations of enzyme (5 mg/ml, buffered at pH 7.0) were incubated at 10, 20, 30, 40, 50, 60 or 70° C. for various times and subsequently assayed for the ability to release amino acids and peptides from bovine casein (available from Bio-Rad Laboratories, Inc., Hercules, Calif.) after 20 hours incubation at pH 7.0. At 60° C., the preparation has a half-life in excess of 6 h; at 50° C., the half-life is well in excess of 24 h; and, at 40° C., the half-life is about 6 days. FIG. 2 displays a profile of the activity of the poly-enzyme preparation at various temperatures. The temperature optimum is 55° C. FIG. 3 displays a profile of the activity of the poly-enzyme preparation after incubation at room temperature at various pH values. Following the incubation, the pH was adjusted to about pH 7.0, and the remaining activity determined as described above. The optimum stability is achieved at about pH 7.0. However, at least 50% of the original activity is retained following about 18 h incubations in solutions having pH values between about 5.0 and about 9.5.

The multifunctional enzyme can be purified from tissue homogenates of fish or crustaceans or from homogenates or supernates derived from a cell culture of transformed or normal prokaryotic or eukaryotic cells that produce the multifunctional enzyme. The preferred purification comprises the use of an affinity column comprising an inhibitor reactive with the multifunctional enzyme. After the multifunctional enzyme is eluted from the affinity column, residual enzyme inhibitor in the preparation is removed. One method of removal is to pass the preparation over an affinity matrix comprising a molecule, typically a protease, with which the inhibitor binds strongly (for instance, with an affinity constant of at least about $10^6$ M, preferably at least about $10^7$ M). More preferably, the affinity ligand is a previously isolated preparation of the multifunctional enzyme that the procedure seeks to purify.

Some amount of traditional protein purification will preferably be done prior to the affinity chromatography step. This can include differential precipitation, gel filtration chromatography, ion-exchange chromatography, chromatography on weakly hydrophobic matrices such as dye matrices, chromatofocusing and reversed phase liquid chromatography. Preferably, these one or more steps will be sufficient to remove all proteins, other than the multifunctional enzyme, that bind to the affinity ligand. Alternatively or supplementally, one or more traditional protein purification steps can be applied after the affinity chromatography step.

A preferred purification procedure comprises the steps of:
(a) applying a composition containing the multifunctional enzyme to an ion exchange column;
(b) eluting a first adsorbed material from the column with a first aqueous solution of selected ionic strength $I_1$; and
(c) eluting the multifunctional enzyme from the column with a second aqueous solution of selected ionic strength $I_2$; and wherein $I_1$ is selected so that the first aqueous solution (i) elutes the first adsorbed material containing proteins that can bind to the hydrolase inhibitor, but which proteins adhere to the anion exchange column more weakly than the multifunctional enzyme and (ii) not elute the multifunctional enzyme, and wherein $I_2$ is greater than $I_1$ and is selected so that the second aqueous solution elutes the multifunctional enzyme and substantially no other proteins that bind a selected protease inhibitor.

The method also further comprises the steps of, after step (c):
(d) applying the eluted multifunctional enzyme from step (c) to an affinity matrix comprising the protease inhibitor;
(e) eluting the affinity matrix with a third aqueous solution that destabilizes the interaction between the multifunctional enzyme and the protease inhibitor; and
(f) collecting the eluted multifunctional enzyme.

These preferred methods surprisingly yield, after a few steps, homogeneous preparations of multifunctional enzyme.

The method optionally comprises the steps of, after step (f):
(g) applying the second eluted solution to an affinity matrix having a prior preparation of the multifunctional enzyme; and
(h) collecting the effluent from the enzyme-containing affinity matrix, the effluent comprising the purified multifunctional enzyme.

Preferably, $I_1$ is about the ionic strength of 0.4M NaCl and $I_2$ is about the ionic strength of 0.6 M NaCl. Preferably, the anion exchange chromatography is conducted at a pH between about 5.5 and about 7.5, more preferably between about 6.0 and about 7.0, yet more preferably about 6.2. Preferably, the anion exchange matrix comprises a polysaccharide-based matrix comprising, in the swelled state, between about 0.05 mmol and about 0.6 mmol anion exchange sites per ml. Preferably, the matrix is a cross-linked dextran of the type sold under the tradename Sepharose. Preferably, the anion exchange groups comprise diethylaminoethyl (DEAE) or quaternaryaminoethyl (QAE) groups, more preferably DEAE groups.

The affinity chromatography of steps (d)-(f) preferably further comprise, between steps (d) and (e), washing the inhibitor-containing column with a solution having ionic strength of at least about that of 0.5 M NaCl, more preferably of about 0.8 M NaCl, yet more preferably of about 1M NaCl. This step and the prior eluting step will preferably be conducted at a pH between about 5.5 and about 7.5, preferably between about 6.0 and about 7.0. The eluting step (e) preferably comprises applying a buffer having pH of about 2 to about 4, preferably about 3. Alternately, it may preferably comprise applying a buffer having pH of at least about 8. The eluting buffer will preferably have sufficient ionic strength to suppress weak ionic interactions with the affinity matrix.

Steps (g) and (h) of the method will preferably be conducted at a pH between about 5.5 and about 7.5, more preferably between about 6.0 and about 7.0. The buffer used in these steps will preferably have sufficient ionic strength to suppress weak ionic interactions with the affinity matrix.

The matrix used to create the affinity matrices will preferably comprise a carbohydrate matrix such as cross-linked dextran (e.g., that sold under the tradename Sepharose) or agarose (e.g., that sold by Pharmacia, Sweden as "Sephacryl"). The matrix should have pore sizes sufficient to admit both the affinity ligand that will be attached to the matrix and the multifunctional enzyme of the invention. Methods of synthesizing appropriate affinity columns are well known. See, for instance, Axén et al., *Nature*, 214:1302-1304, 1967.

Preferably, the affinity ligand is selected to be resistant to digestion by the multifunctional enzyme under the conditions used in steps (d) and (e). Such affinity ligands include bovine trypsin inhibitor. Using such an inhibitor, optional steps (g) and (h) are generally of less importance.

Isolations and partial sequences of various fish or crustacean hydrolases have been reported. A number of such reports are identified in Table 1, below.

TABLE 1

| Sequence Reports |  |
| --- | --- |
| *Penaeus vanamelii* 1 | |
| Sequence reported: | Van Wormoudt et al., Comp Biochem. Physiol., 103B: 675–680, 1992 and Sellos and Wormhoudt, FEBS, 39: 219–224, 1992. |
| Reported activities: | chymotryptic |
| Apparent MW: | 25 kd |
| *Panaeus vanameii* 2 | |
| Sequence reported: | Van Wormoudt et al., Comp Biochem. Physiol., 103B: 675–680, 1992. |
| Reported activities | chymotryptic (tryptic) |
| Apparent MW: | 25 kd |

TABLE 1-continued

| Sequence Reports |  |
| --- | --- |
| *Panaeus monodon* tryptic (shrimp) | |
| Sequence reported: | Lu et al., Biol. Chem. Hoppe-Seyler, 371: 851–859, 1990. |
| Reported activities: | tryptic |
| Apparent MW: | 27 kd |
| Ph optimum: | 7.4–8.0 |
| Pi: | ≦2.4 |
| *Panaeus monodon* chymotryptic - 1 (shrimp) | |
| Sequence reported: | Tsai et al., Biochem et Biophys. Acta, 1080: 59–67, 1991 |
| Reported activities: | chymotryptic collagenase |
| Apparent MW: | 27–28 kd |
| *Panaeus monodon* chymotryptic - 2 | |
| Sequence reported: | Tsai et al., Biochem. et Biophys. Acta, 1080: 59–67, 1991 |
| Reported activities: | chymotryptic collagenase |
| Apparent MW: | 25–26 kd |
| *Uca pubilator* (Fiddler Crab) 1 | |
| Sequence reported: | Tsai et al., Biochem. et Biophys. Acta, 1080: 59–67, 1991 |
| Reported activities: | chymotryptic |
| Apparent MW: | 25 kd |
| Ph optimum | 8.0–8.5 |
| *Uca pugilator* II | |
| Sequence reported: | Grant et al., Biochemistry, 19: 4653–4659, 1980. |
| Reported activities: | chymotryptic collagenase tryptic elastase |
| Apparent MW: | 25 kd |
| pI: | 8.0–8.5 |
| Kamchatka crab (at least four proteases) | |
| Sequence Reported: | Grant et al., Biochemistry, 22: 354–358, 1983 |
| Reported Activities: | tryptic collagenase |
| Apparent MW: | 23–26 kd |
| Crayfish Protease | |
| Sequence reported: | Titani et al., Biochemistry, 22: 1459–1465, |

The sequence of the first 25 amino acids of the Krill derived multifunctional enzyme is I-V-G-G-N/M-E-V-T-P-H-A-Y-P-(W)-Q-V-G-L-F-I-D-D-M-Y-F (SEQ ID NO. 1). The parentheses indicate a weak recovery of the 14th 25 amino acid and "N/M" indicates heterogeneity at the 5th position. A comparison of the N-terminal 20 to 25 amino acid sequences of various serine hydrolases is presented in Table 2, below.

TABLE 2

N-Terminal Sequences

| Species | SEQ ID NO | Sequence |
|---|---|---|
| *Penaeus vanameii* 1 (shrimp) | 3 | I V G G V E A T P H S W P H Q A A L F I D D M Y F |
| *Penaeus vanameii* 2 | 4 | I V G G V E A T P H S X P H Q A A L F I |
| *P. monodon*, trypt. (shrimp) | 5 | I V G G T A V T P G E F P Y Q L S F Q D S I E G V |
| *P. monodon*, chym. 1 | 6 | I V G G V E A V P G V W P Y Q A A L F I I D M Y F |
| *P. monodon*, chym. 2 | 7 | I V G G V E A V P H S W P Y Q A A L F I I D M Y F |
| *Uca pugilator* I (crab) | 8 | I V G G V E A V P N S W P H Q A A L F I D D M Y F |
| *Uca pugilator* II | 9 | I V G G Q D A T P G Q F P Y Q L S F Q D |
| King crab | 10 | I V G G Q E A S P G S W P ? Q V G L F |
| Kamchatka crab | 11 | I V G G Q E A S P G S W P X Q V G L F F |
| | 12 | I V G G T E V T P G E I P Y Q L S L Q D |
| | 13 | I V G G T E V T P G E I P Y Q L S F Q D |
| | 14 | I V G G S E A T S G Q F P Y Q X S F Q D |
| Crayfish | 15 | I V G G T D A T L G E F P Y Q L S F Q N |
| krill Enzyme | 1 | I V G G N E V T P H A Y P W Q V G L F I D D M Y F |
| | 2 | I V G G M E V T P H A Y P W Q V G L F I D D M Y F |
| Bovine chymotrypsn | 16 | I V N G E D A V P G S W P W Q V S L Q D |
| Salmon | 18 | I V G G Y E C K A Y S Q A Y Q V S L N S G Y H Y C |
| Atlant. Cod | 19 | I V G G Y E C T K H S Q A H Q V S L N S G Y H Y C |
| Atlantic Cod | 20 | I V G G Y E C T R H S Q A H Q V S L N S G Y H Y C |

X = unknown or undefined.

It will be apparent to those of ordinary skill that the enzyme can be manufactured by recombinant means. For instance, the sequences recited herein can be used as the basis of oligonucleotide probes for screening expression or genomic libraries to isolate the complete structural gene. See, e.g., Suggs et al., *Proc. Natl. Acad. Sci. USA,* 78: 6613, 1981 or Berent et al., *BioTechniques,* 3: 208, 1985. Alternately, known protein sequences can be used to design primers for use in PCR-based amplification of nucleic acid encoding a multifunctional enzyme. See generally, *Molecular Cloning: A Laboratory Manual*, second edition, Cold Spring Harbor, 1989 and *PCR Protocols, A Guide to Methods and Applications*, edited by Michael et al., Academic Press, 1990. Once fully identified, these structural genes can be edited and appropriately inserted into expression vectors by methods known to the art.

These structural genes can be altered by mutagenesis methods such as that described by Adelman et al., *DNA,* 2: 183, 1983 or through the use of synthetic nucleic acid strands. The products of mutant genes can be readily tested for multifunctional enzymic activity. Conservative mutations are preferred. Such conservative mutations include mutations that switch one amino acid for another within one of the following groups:

1. Small aliphatic, nonpolar or slightly polar residues: Ala, Ser, Thr, Pro and Gly;
2. Polar, negatively charged residues and their amides: Asp, Asn, Glu and Gln;
3. Polar, positively charged residues: His, Arg and Lys;
4. Large aliphatic, nonpolar residues: Met, Leu, Ile, Val and Cys; and
5. Aromatic residues: Phe, Tyr and Trp.

A preferred listing of conservative substitutions is the following:

| Original Residue | Substitution |
|---|---|
| Ala | Gly, Ser |
| Arg | Lys |
| Asn | Gln, His |
| Asp | Glu |
| Cys | Ser |
| Gln | Asn |
| Glu | Asp |
| Gly | Ala, Pro |

-continued

| Original Residue | Substitution |
|---|---|
| His | Asn, Gln |
| Ile | Leu, Val |
| Leu | Ile, Val |
| Lys | Arg, Gln, Glu |
| Met | Leu, Tyr, Ile |
| Phe | Met, Leu, Tyr |
| Ser | Thr |
| Thr | Ser |
| Trp | Tyr |
| Tyr | Trp, Phe |
| Val | Ile, Leu |

The types of substitutions selected can be based on the analysis of the frequencies of amino acid substitutions between homologous proteins of different species developed by Schulz et al., *Principles of Protein Structure*, Springer-Verlag, 1978, pp. 14-16, on the analyses of structure-forming potentials developed by Chou and Fasman, *Biochemistry* 13, 211, 1974 or other such methods reviewed by Schulz et al, *Principles in Protein Structure*, Springer-Verlag, 1978, pp. 108-130, and on the analysis of hydrophobicity patterns in proteins developed by Kyte and Doolittle, *J. Mol. Biol.* 157: 105-132, 1982.

Clinical trials with patients suffering from post-partum hemorrhoids have shown that 1 ml of hydrogel (of Example 1F) containing 500 μg/ml of the krill-derived hydrolase of Example 1C applied to the hemorrhoids three times daily is effective to cure the hemorrhoid outbreak within two days, and usually within one day.

A double blind, placebo controlled trial with patients suffering from genital herpes has shown that 1 ml of hydrogel (of Example 1F) containing 500 μg/ml of the krill-derived hydrolase of Example 1C applied three times daily is effective to heal the sores of the herpes outbreaks within an average of 5 days. In patients treated with placebo, the outbreaks lasted an average of 12 days. In the patients treated with the hydrolase, pain and itching were gone within 36 hours, while these symptoms peaked at day 3 or 4 in the placebo controls.

Clinical trials with HIV patients suffering from oral candida have shown that a lozenge (of Example 1H) containing 3 mg of the krill-derived hydrolase of Example 1C applied three times daily is effective to clear the infection within 7 to 9 days.

Clinical trials with patients suffering from recurrent vaginal *candidiasis* that is resistant to traditional antifungal drugs have shown that 1 ml of hydrogel (of Example 1F) containing either 100 μg/ml or 250 μg/ml of the krill-derived hydrolase of Example 1C applied three times daily is effective to clear the candida outbreak within an average of four days and to reduce the recurrence rate.

A topical methicillin-resistant *Staphylococcus aureus* ("MRSA") infection characterized by necrotic tissue, erythematous and underlying tissues that were distended and edematous and affecting an approximately 100 cm² area has been effectively treated by applying 3 ml of hydrogel (of Example 1F) containing 500 μg/ml of the krill-derived hydrolase of Example 1C three times daily. After application, the infection was covered by a dressing. By the third treatment on the second day, all necrotic tissue was removed, the erythema substantially reduced, and exudate flowed from the affected tissue. By day five, the edema was gone. By day seven, the wound was 40% closed, and the MRSA culture was negative. By day nine, the wound was 75% healed.

Krill, including without limitation krill of the genuses *Euphasia* (such as *superba, crystallorphias, frigida, triacantha, vellantini, lougirostris, lucens, similis, spinifera, recurva* and the like), *Meganyctiphanes* (such as *norvegica* and the like) and *Tysanoessa* (such as *macurura, vicina, gregaria* and the like), are a preferred source of the multifunctional enzyme.

The invention is exemplified with the following nonlimiting examples. Although in all of the examples the multifunctional enzyme derived from krill (i.e., the krill multifunctional hydrolase) was used, other multifunctional enzymes can be employed.

Example 1A

Poly-Enzyme Preparation

Frozen krill were thawed and homogenized. An equal volume of distilled water containing 0.02% (w/v) sodium azide was added, and the admixture stirred for about 6 hours at about 4° C. Then, the supernate was collected by centrifugation. The supernate was defatted by adding ethyl acetate and stirring overnight at 4° C. The fat-containing ethyl acetate layer was then decanted and the aqueous extract evaporated sufficiently to remove the ethyl acetate. Ammonium sulfate was added to the extract to about 60% saturation at about 4° C. and the mixture stirred overnight. The salted out precipitate was isolated by centrifugation. The precipitate was dissolved in phosphate buffered saline ("PBS", 0.05 M sodium phosphate, pH 7.4, 0.05 M sodium chloride) and dialyzed (using a 10 kd molecular weight cutoff) against PBS.

The redissolved precipitate was applied to a cross-linked agarose gel filtration column (Sephacryl 200, Pharmacia, Sweden) and the fractions displaying absorbance at about 280 nm were assayed for proteolytic activity. The combined proteolytically active fractions were pooled and lyophilized. A "poly-enzyme" preparation containing about six bands with apparent molecular weights (by SDS PAGE) ranging from 24 to 34 kd were isolated from antarctic krill in this way. For storage, a lyophilized powder of this preparation was aliquoted into ampules at 25 Casein Units per ampule.

Example 1B

Preparation of Krill-Derived Multifunctional Enzyme

A poly-enzyme preparation prepared as described in Example 1A was reapplied to a Sephacryl 200 column. A fraction that was substantially homogeneous and displayed an apparent molecular weight of 29 kd was isolated. This fraction was found, using the proteolysis assays described below, to have multifunctional activity. The lyophilizate of this krill-derived multifunctional enzyme was placed into ampules at: 15 Casein Units per ampule for sterile storage without preservatives or anti-microbial additives.

Example 1C

Multifunctional Enzyme Purification

A 100 kg of frozen antarctic Krill were thawed, and mixed with 100 kgs of distilled water, and stirred for 30 minutes. The krill used were harvested in the January through March period. During this period, krill are largely without pigment and are called "white" krill. (Due to dietary changes, later in the season krill are harvested as "red" krill. Multifunctional hydrolase yields from red krill are 30 to 40% less than from white krill. Still later in the season, during June through August, "black" krill are harvested. Black krill yield still less enzyme.) The supernate was collected by centrifugation using a GL-sieve, starch centrifuge (Model 220, available from G. Larssons Mekaniska Verkstad, Fjälkinge, Sweden) using a 125 micron spinning cone at 1,000 rpm. The pH of the supernate was adjusted to 6.2. The supernate had turbidity of less than 4% and fat content of less than 2%.

The supernate, 100 mls, was further clarified by centrifugation at 17,000×g and mixed with 5 kg of DEAE-sepharose gel (Pharmacia, Sweden), which had been previously been equilibrated to pH 6.2. The mixture was stirred gently for 1 hour. The gel was collected on a filter bed and washed with 5 volumes of 0.4 M NaCl. The gel was then packed into a suitable column container using a 0.4 M NaCl saline solution. The column was then washed overnight with 15 bed volumes of 0.4 M NaCl.

A protein containing fraction (approximately 1.5 liters collected) was desorbed from the gel with 0.6 M NaCl. This fraction contained multiple proteins with molecular weights ranging from 10 kd to greater than 90 kd, as determined by SDS-PAGE. The protein content was 20 g/l, as determined by absorbance at 280 nm. The protein fraction was filter sterilized through a 0.20 micron filter and applied to an affinity column comprising soybean trypsin inhibitor coupled to agarose (200 ml of gel, substitution ratio 3:1 gel:inhibitor). The affinity gel was washed with 4 bed volumes of 1 M NaCl. The multifunctional enzyme was desorbed from the gel with 0.2 M sodium citrate, pH 3.0. (In parallel procedures, equivalent preparations of a multifunctional enzyme were prepared by using either 0.5 M TRIS-HCl, pH 8.0 or 0.1 M ammonium solution, pH 11 to desorb the multifunctional hydrolase). The yield of multifunctional enzyme was 100 mg.

The multifunctional hydrolase preparation was adjusted to pH 7.4 and applied to 200 ml of an agarose affinity gel to which a prior preparation of the multifunctional enzyme had been coupled (6:1 substitution ratio gel:enzyme).

The purified multifunctional hydrolase preparation was homogeneous by SDS-PAGE. The purified preparation was filter sterilized and aliquoted into injection vials. The injection vials were freeze dried. The freeze-dried powder is stable when stored at 4° C.

Example 1D

Protein Characterization

The krill-derived multifunctional hydrolase was purified by the protocol described above in Example 1C. Three preparations the krill-derived multifunctional hydrolase were prepared. The three preparations differed only in that the krill multifunctional hydrolase was eluted from the trypsin inhibitor gel with buffer at pH 3, pH 8, and pH 11, respectively. These preparations shall be termed "Prep-3," "Prep-8," and "Prep-11." These preparations were dissolved in water to a concentration of 6 mg/ml.

Samples of each preparation were analyzed by SDS-PAGE, and each preparation was found to contain a single protein that banded with apparent molecular weight of 29 kd. The SDS bands were electroblotted onto PVDF membranes and sequenced through 25 cycles of Edman degradation. See, Matsudaira, *J. Biol. Chem.*, 262: 10035-10038, 1987. Each preparation yielded the identical sequence: I V G G M/N E V T P H A-Y P W Q V G L F I D D M Y F (SEQ ID NO. 1). Accordingly, it is clear that all three preparations are homogenous, although each is micro-heterogeneous at position 5. The proteolytic activity of each of the three preparations was tested against substrate benzoyl-val-gly-arg-p-nitroaniline.

Figure 9:
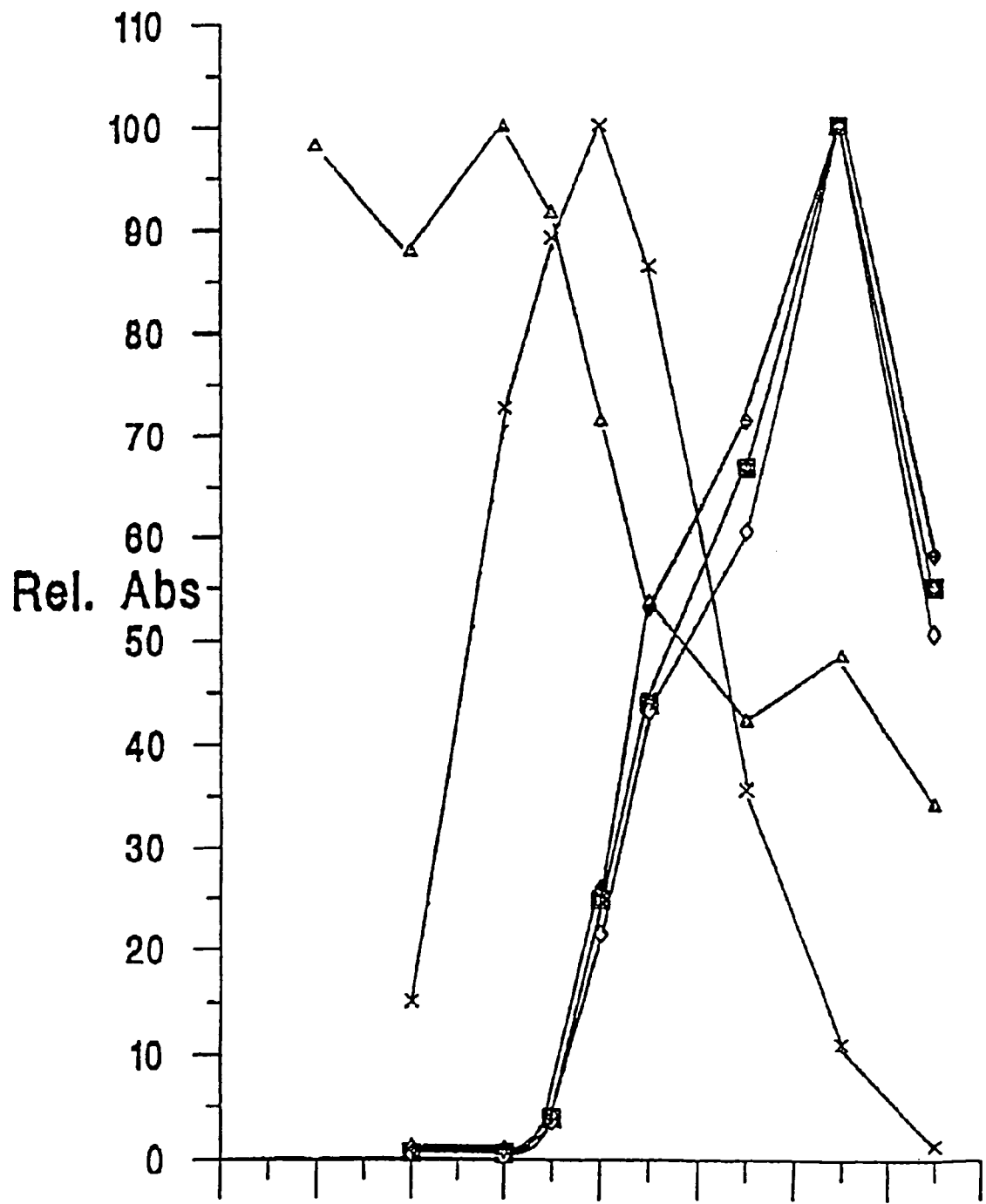
FIG. 9 shows the pH dependence of the multifunctional enzyme, purified as described in Example 1C, when tested against different substrates.

Hydrolysis of this substrate can be monitored at 210 nm, reflecting the release of p-nitroaniline. The pH-dependence of the three preparations at an ionic strength of 0.1 M is shown in FIG. 9. The profile for Prep-3 (shown with filled squares), Prep-8 (shown with open diamonds) and Prep-11 (shown with filled diamonds) are identical. All three had a pH optimum for this substrate of 9.5.

With the elastase substrates succinyl-p-ala-pro-ala-p-nitroanilide and boc-ala-ala-pro-ala-p-nitroanilide, the pH optimum for Prep-8 was 7.0. See the profile in FIG. 9, represented by the X's. Similar model substrate studies determined that the order of cleavage efficiencies for the krill multifunctional hydrolase is chymotrypsin≧trypsin≧elastase.

For the substrate azocasein, the profile for pH dependence was broad and in the acidic pH region. See the profile in FIG. 9, represented by the open triangles.

$K_m$ values were determined using benzoyl-pal-gly-arg-p-nitroanilide in 0.1 M in CAPS buffer containing 2 mM $Ca^{++}$ at pH 9.5. The $K_m$ values for Prep-3, Prep-8 and Prep-11 were 210±8, 210±8 and 230±13 µM, respectively. Against the substrate succinyl-ala-ala-pro-phe-p-nitroanilide, under the same conditions, the $K_m$ values were 260±50, 270±50 and 270±40 µM, respectively.

The effectiveness of three protease inhibitors was tested at pH 9.5 against the three hydrolase preparations. The results were as follows:

| Protease inhibitor | Prep-3 | Prep-8 (% ACTIVITY REMAINING) | Prep-11 |
|---|---|---|---|
| Antipain (1 µM) | 2 | 5 | 5 |
| Chymostatin (1 µM) | 0 | 0 | 0 |
| Bovine pancreatic trypsin inhibitor (1 µM) | 2 | 1 | 1 |

The effectiveness of other protease inhibitors against Prep-8 was tested in a 0.1 M Tris-HCl buffer pH 7.5. Benzoyl-val-gly-arg-p-nitroanilide ("ARG-p-NA") and succinyl-ala-pro-phe-p-nitroanilide (Phe-pNA) were used as substrates. The results were as follows:

| | Substrate: | |
|---|---|---|
| Inhibitor: | Phe-pNA | Arg-pNA |
| | (Activity remaining, %) | |
| Phosphoramidon (10 µM) | 94 | 87 |
| Elastatinal (10 µM) | 100 | 100 |
| Eglin C fragment (8.4 µM) | 100 | Not done |
| Anti-Thrombin III (0.2 µM) | 2 | 4 |
| α-anti-chymotrypsin (0.2 µM) | 1 | 7 |
| α-proteinase inhibitor (0.2 µM) | 0 | 0 |

Figure 10:
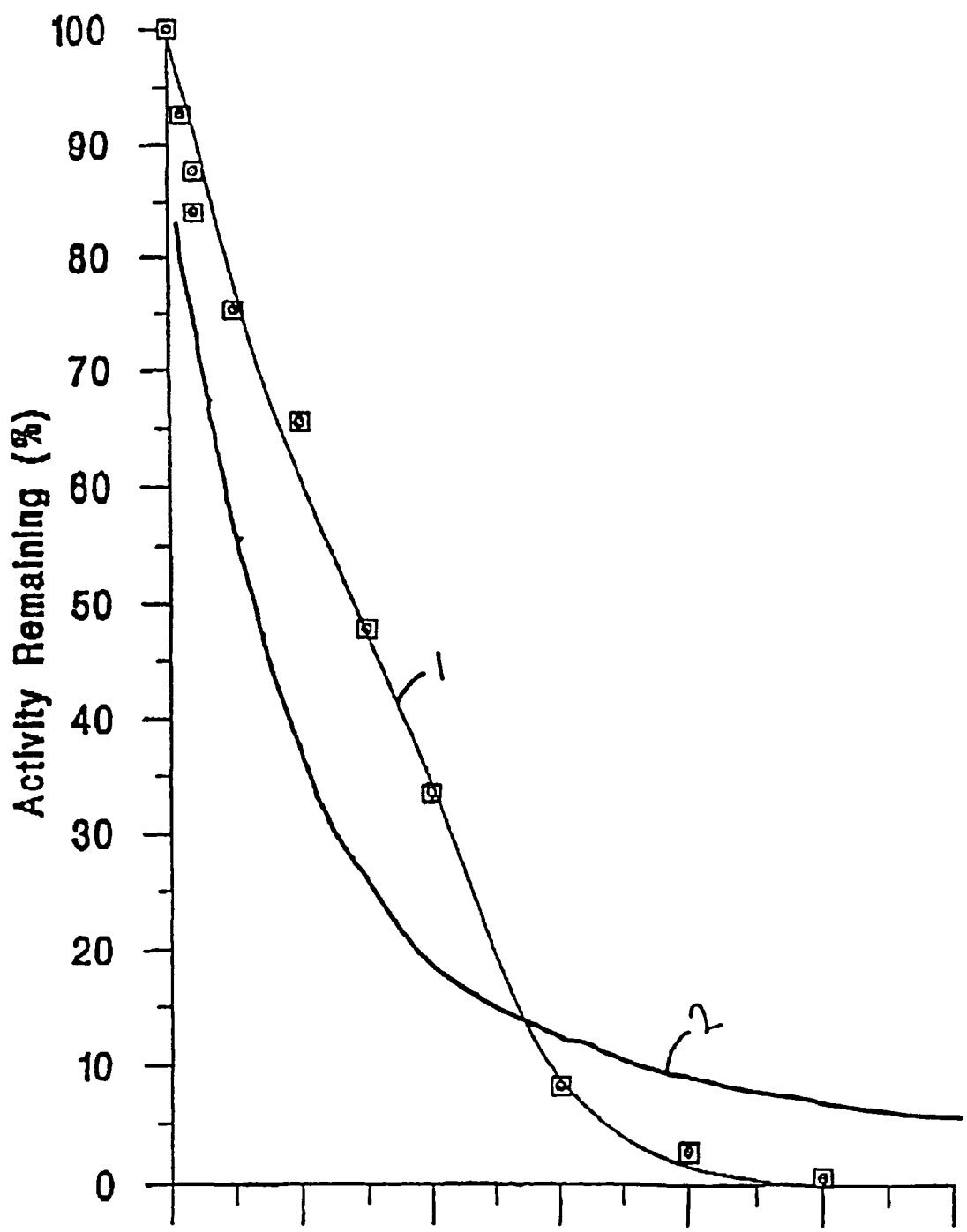
FIG. 10 shows the titration of the activity of the multifunctional enzyme, purified as described in Example 1C, with 2 different protease inhibitors.

Aliquots of a solution of Prep-8, with a nominal concentration of 6 mg/ml, were titrated against either bovine pancreatic trypsin inhibitor, $α_1$-antichymotrypsin, α-protease inhibitor and soybean trypsin inhibitor. The results are displayed in FIG. 10. Profile 1 is for a titration of bovine pancreatic trypsin inhibitor tested at pH 9.5 using benzoyl-val-gly-arg-p-nitroanilide as the substrate. For profile 2, the pH was 7.0 and the substrate used was succinyl-ala-ala-pro-phe-p-nitroanilide. Similar profiles have been obtained with α-antichymotrypsin, α-protease inhibitor and soybean trypsin inhibitor. These curves can be used to estimate the $K_i$ for the inhibitor and the effective concentration of multifunctional hydrolase.

Example 1E

Hydrogel Preparation

The multifunctional enzyme is mixed with a hydrogel made up of low molecular weight hydrolyzed starch containing 90% water by methods known in the art to obtain a hydrogel formulation of the enzyme.

Example 1F

Hydrogel Preparation

The multifunctional hydrolase according to Example 1B was mixed with hydrocolloid gel comprising an aqueous gel containing 0.8% w/v Carbopol™ (Dow Corning, Midland, Mich.) and 23.5% w/v glycerin prior to use. (Carbopol™ is a vinyl polymer with active carboxy groups described in *Chem. Eng. News* 36:64 (1958).)

Example 1G

Hydrogel Preparation

The multifunctional enzyme according to Example 1C was mixed with hydrocolloid gel comprising an aqueous gel containing 0.8% w/v Carbopol™ (Dow Corning, Midland, Mich.), 23.5% w/v glycerin and 10% w/v Pluronic P85 (BASF, Wyandotte, Mich.) prior to use. (Carbopol™ is a vinyl polymer with active carboxy groups. *Chem. Eng. News* 36:64 (1958).)

Example 1H

Lozenge Preparation

Lozenges containing 3 or 6 mg of the multifunctional enzyme according to Example 1C were formed from 50% lactose, 20%, Avicel (microcrystalline cellulose), 29% sucrose and 1% magnesium stearate.

Example 2

Protease Activity

The multifunctional enzyme is compared to isolated krill multifunctional protease for molecular weight, sequence, temperature or pH stability, temperature or pH optima and proteolytic specificity.

Example 2A

Specificity

To study proteolytic specificity, the following substrates are used:

| Substrate | Type of Activity |
|---|---|
| Succinyl-Ala-Ala-Pro-Phe-pNO$_2$ anilide | Chymotrypsin |
| Boc-Ala-Ala-Pro-Ala-pNO$_2$ anilide | Elastase |
| Benzoyl-Val-Gly-Arg-pNO$_2$anilide | Trypsin. |

These substrates are used to measure the proteolytic activities of the multifunctional enzyme in accordance with Example 1D. See, *Biochemical J.*, 185:423-33, 1980; *J. Biol. Chem.*, 269:19565-19572, 1994. These studies include measurements of $K_m$ and $K_{cal}$.

Example 2B

Exo Peptidase Activity

The krill multifunctional hydrolase purified as in Example 1B (1 mg) was dissolved in 5 ml buffer together with 1% (wt/v) bovine casein and incubated at 20° C. for 24 hours. The buffer was 0.1M sodium phosphate, pH 7.5. After 24 hours, 10% trichloroacetic acid was added to precipitate the proteins present in the solution. The supernate was collected and reacted with ninhydrin. The ninhydrin was used from a 2% solution in 3:1 DMSO: 4M Lithium Acetate, pH 5.2, as instructed by the supplier, Sigma Chemical, Co., St. Louis. The reacted supernate was applied to a cross-linked acrylamide column (Biorad P-2, Bio-Rad, Hercules, Calif.) to separate reacted amino acids from reacted peptides. The concentration of amino acids in the amino acid fraction was determined from the absorbance at 820 nm. A 1% solution of undigested casein was treated in the same way as a control. The control had an absorbance of less than 0.01, while the amino acid fraction of the digest displays an absorbance of 0.28 (at equivalent dilutions).

Example 2C pH Optima

The multifunctional enzyme is tested for proteolytic activity against various substrates in solutions having various pH values between 4 and 10 to determine the pH optima against a given substrate, using buffer conditions that are well known in the art. These optima can be compared to the corresponding optima for the krill multifunctional hydrolase.

Example 2D

Protease Inhibitors

The effectiveness of various protease inhibitors is used to examine the relatedness of the various candidate multifunctional enzymes. These inhibitors are $\alpha_1$-protease inhibitor, $\alpha_1$-antichymotrypsin, anti-thrombin III, $\alpha_2$-macroglobin, bovine pancreas protein inhibitor, and soybean protein inhibitor. Conditions for conducting such studies are described in Example 1D. These inhibitors are available from Sigma Chemical Co, St. Louis, Mo. $K_i$ values are determined in solutions of various pHs using the following protease substrates, including TAME, Benzoyl-Val-Gly-Arg-p-NO$_2$-anilide, Succinyl-Ala-Ala-Pro-Phe-p-NO$_2$-anilide, Boc-Ala-Ala-Pro-Ala--p-NO$_2$-anilide and azocasein.

Example 3A

In Vitro Binding of HL60 Cells to Endothelial Cells

Endothelial cells were first passaged onto 96 well plates at a given concentration. The endothelial cells used in the experiment are described in Edgell et al., *Proc. Natl. Acad. Sci. USA* (1983) 80:3734. The cells were incubated at 37° C. under a DMEM cell culture medium containing 10% fetal calf serum and under a 5% CO$_2$ atmosphere. Then, the medium was removed and replaced with 100 µl of a suspension of 200,000 HL60 cells (a human lymphocyte cell line, available from the European Cell Culture Bank under ECACC Accession No. 85011431) in RPMI medium containing 10% fetal calf serum. The cells were incubated for 30 minutes. After this, the medium was removed and the adherent cells were washed two times with DMEM medium. The relative adherence of the HL60 cells was measured by measuring the difference in optical density at 450 nm between the plates on which the cells were co-incubated and plates having endothelial cells alone.

The effect of TNFα was measured by adding TNFα at 1500 units/ml to the endothelial cells 4 hours before the incubation with HL60 cells. The effect of antibody to E-selectin was measured by adding 25 µg/ml of monoclonal antibody BBAZ (R&D Systems Europe, Oxford, England) to the HL60 cells. The results of the experiments were:

| Expt. No. | HL60 Cells | Endothelial Cells | Absorbance* |
|---|---|---|---|
| 1 | no treatment | no treatment | 0.324 |
| 2 | no treatment | pretreated with TNFα | 0.444 |
| 3 | added in the presence of mAb to E-selectin | pretreated with TNFα | 0.357 |

*increase over absorbance of endothelial cells alone

The effects of the krill multifunctional hydrolase on this system were measured by:
(1) measuring the effect of adding to the endothelial cells 92.3 µg/ml krill multifunctional hydrolase (prepared as in Example 1C) together with the HL60 cells;
(2) After pretreating the endothelial cells with TNFα for 2 hours, adding 92.3 µg/ml krill multifunctional hydrolase and incubating for 2 more hours prior to the addition of HL60 cells; or
(3) Pretreating the HL60 cells with 92.3 µg/ml krill multifunctional hydrolase prior to adding the HL60 cells to the plates of endothelial cells.

The results of these experiments were as follows:

| Expt. No. | HL60 Cells | Endoth Cells | Absorbance* |
|---|---|---|---|
| 4 | Multifunctional enzyme added simultaneously with cells | pretreated with TNFα | 0.425 |
| 5 | no treatment | Four hours pretreatment: 0–4 h TNFα 2–4 h multifunctional enzyme | 0.247 |
| 6 | pretreated with multifunctional enzyme for 2 h | pretreated with TNFα | 0.160 |
| 7 | pretreated with multifunctional enzyme for 2 h | Four hours pretreatment: 0–4 h TNFα 2–4 h multifunctional enzyme | 0.059 |

*increase over absorbance of endothelial cells alone.

To confirm these results, the number of adhering HL60 cells were counted by removing them from the plate and counting the cells. The number of HL60 cells was determined by subtracting the cell numbers for control plates having only endothelial cells. These counting results mirrored the optical density results, as follows:

| EXPERIMENT | HL60 CELL NUMBER |
|---|---|
| 1 | 32,590 |
| 2 | 43,990 |
| 3 | 35,730 |
| 4 | 42,190 |
| 5 | 25,280 |
| 6 | 17,010 |

These adherence studies show that krill hydrolase destroyed the cell-surface ligand and acceptor molecules that facilitate cell-adhesion.

Example 3B

Activity Against Certain Cell-Surface Adhesion Molecules

Freshly isolated T-cells from the thymus of a C57BL/6 mouse (bred by Institut Armaud Frappier) were washed three times with serum-free medium. 1 ml aliquots of the cells containing $5-10 \times 10^6$ cells were treated at 37° C. for 4 hours with 0, 100 or 500 µg/ml of the krill-derived multifunctional hydrolase prepared according to Example 1B dissolved in serum-free medium. Resulting cells were labelled with one of fluorescent antibodies identified below:

| Antibody | Source |
|---|---|
| CD4-PE | Boehringer Mannheim, LaVal, Quebec |
| CD8-Red613 | GIBCO, Long Island, New York |
| ICAM-1 | PharMingen, San Diego, CA |
| ICAM-2 | PharMingen, San Diego, CA |
| CD44 | PharMingen, San Diego, CA |
| H-2K | PharMingen, San Diego, CA |

The amount of antibody binding was determined using a fluorescence-activated cell sorter. From the results, it was determined that the order of sensitivity to inactivation or removal by the hydrolase was CD4, CD8<ICAM-2<CD44<ICAM-1<H-2K. Using these same methods with appropriate cells, including endothelial cells, including the s-end-1 endothelial cell line (Kinashi et al., *J. Beukocyte Biol.* 57: 168, 1995) and T-cells isolated from the thymuses of C57BL/6 mice, it was determined that the VCAM-1, CD28, CD 31 and asialo GM1 ceramide markers are sensitive to the hydrolase. The antibodies used to make these determinations were:

| antibody specificity | source |
|---|---|
| VCAM-1 | PharMingen, San Diego, CA |
| CD28 | PharMingen, San Diego, CA |
| CD31 | PharMingen, San Diego, CA |
| asialoGM1 | Wako Bioproducts, Richmond, VA |

In some cases, binding was detected with a labeled second antibody, for instance, binding of the asialo GM1 antibody was detected with FITC-labeled Fab fragments that were specific for rabbit IgG (heavy and light chains), which was obtained from Caltag Laboratories, San Francisco, Calif.

Example 3C

Timecourse of Cell Surface Recovery of Adhesion Molecules

DO-11.10 T cell hybrids (this cell line is described by Shimonkevitz et al., *J. Experimental Med.* 158: 303, 1983) were treated with 500 μg/ml of the krill-derived multifunctional hydrolase prepared according to Example 1B and tested for the CD4 marker as described in Example 3B. Immediately after the treatment, well less than 1% of the amount of CD4 found in the controls was found on the hydrolase-treated cells. 48 hours later, the levels in treated cells were the same as those in untreated cells.

Example 4

Cell Binding Comparisons

The effectiveness of various members of the multifunctional enzyme family, i.e., the non-krill multifunctional enzymes having at least about 60% homology with the krill-derived hydrolase, are compared with that derived from krill using the HL60 binding assay of Example 3A.

Example 5

Figure 4:
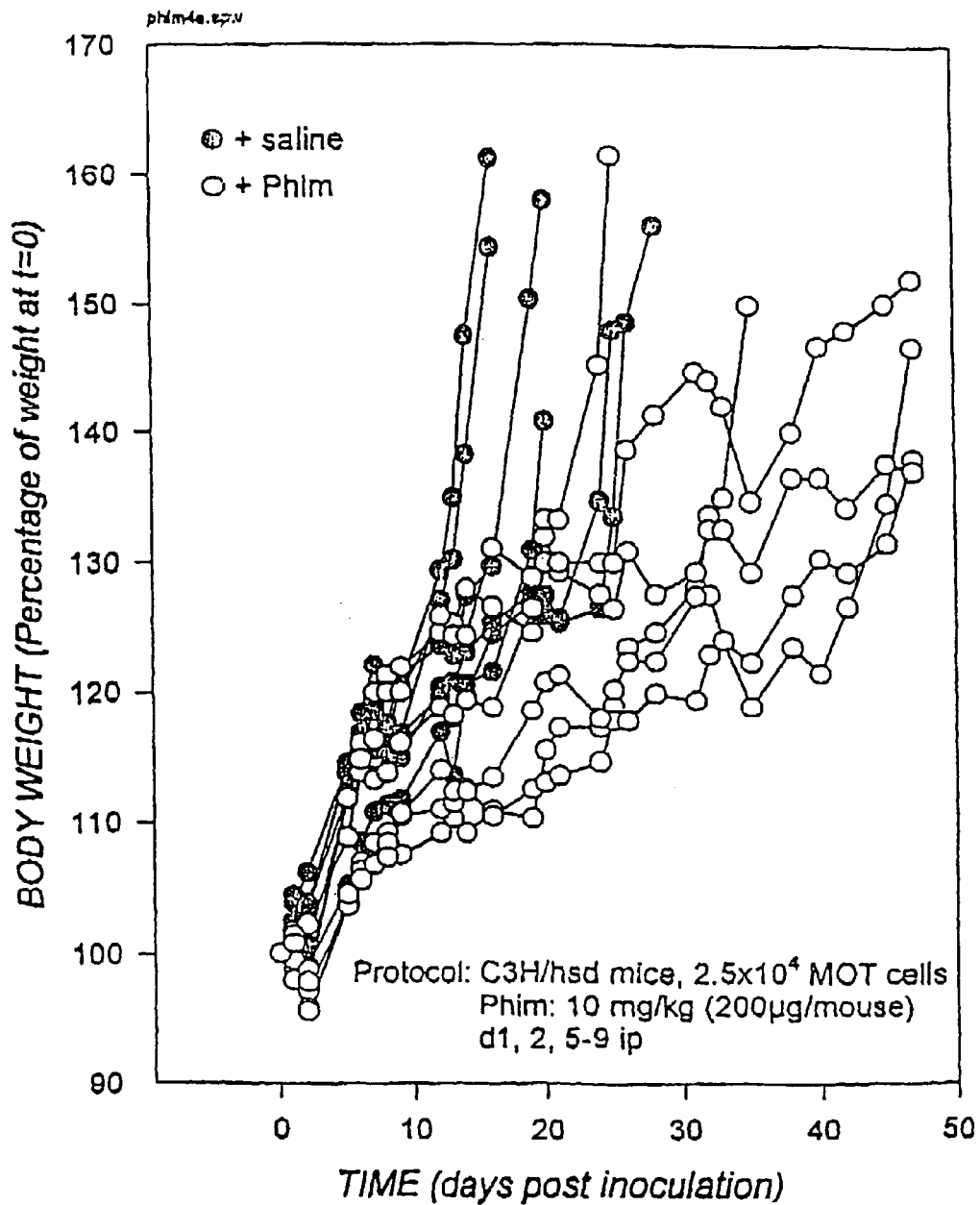
FIG. 4 shows the weight gain of mice having a soft ovarian-derived tumor that were either untreated or treated with the multifunctional enzyme purified as described in Example 1C.
Figure 5:
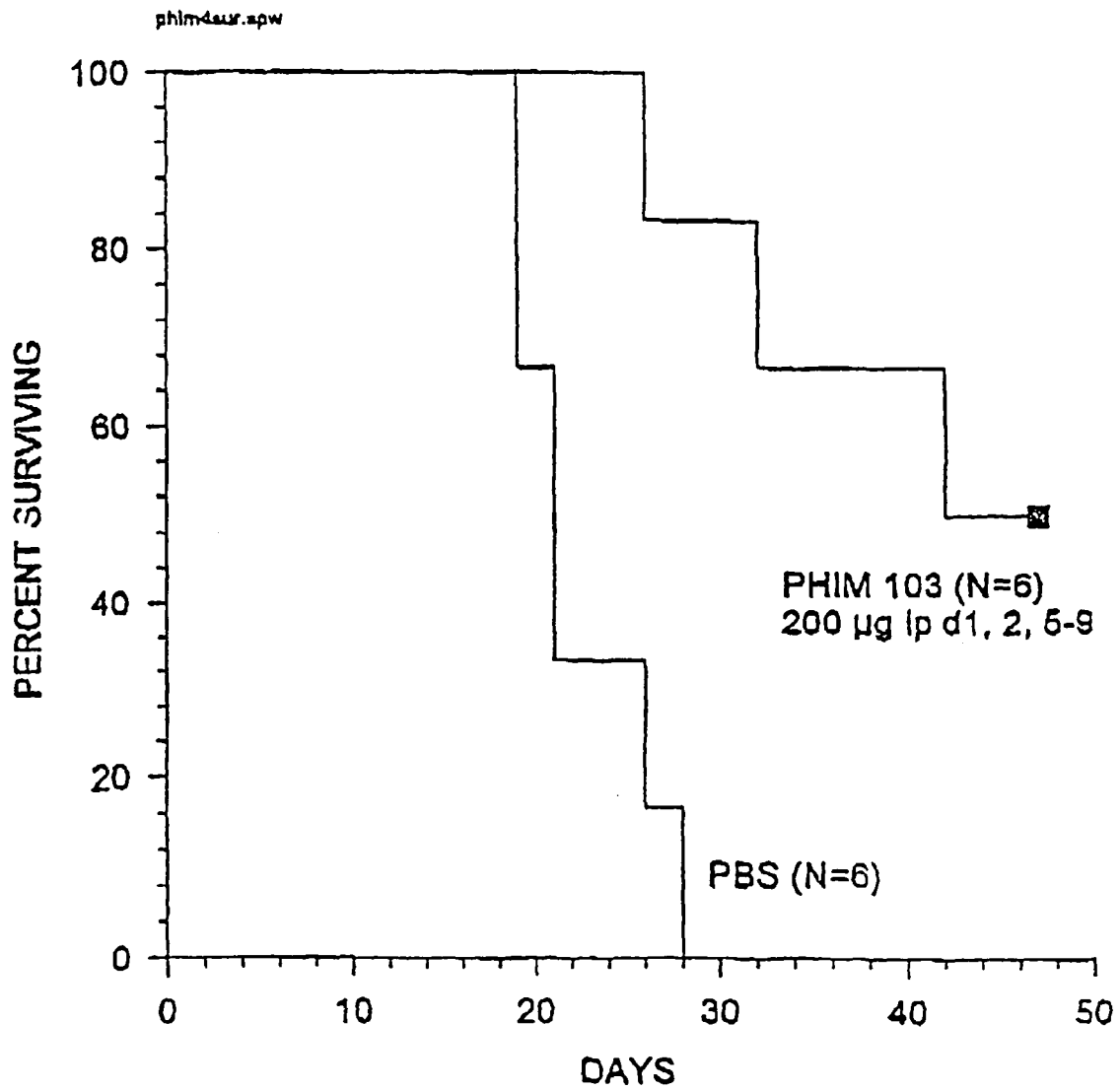
FIG. 5 shows the survival of the enzyme-treated and untreated mice containing the ovarian tumor.

Mouse Ovarian Tumor Treatment 25,000 mouse ovarian tumor cells were injected into the abdominal cavity of 12 C3H/hsd mice). On days 1, 2 and each of days 5-9, 1 ml of either saline or 200 μg of krill multifunctional hydrolase (prepared as described in Example 1C) dissolved in saline was injected into the ascites. In FIG. 4, weight gains (an indication of tumor growth) for saline treated (dark circles) and hydrolase treated (open circles) mice are shown. In FIG. 5, the percentage of the animals surviving over time for saline (line A) and hydrolase (line B) treated mice. Solid tumors formed in the control mice, but not in the enzyme-treated mice.

Tumor cells were recoverable from the ascites fluid of the treated mice. 25,000 such recovered tumor cells were injected into each of 6 C3H/hsd mice. In control experiments, the same number of untreated mouse ovarian tumor cells were injected into C3H/hsd mice. Tumors formed in the control mice, but not in the mice injected with recovered cells.

Example 6A

Toxicology

Separate groups of male and female rats (Crl:CD(SD) BR strain, Charles River Ltd, Margate, UK; 5 rats per group) were treated by the I.V. route with 0, 0.5, 5 and 50 mg/kg per day of the Krill-derived multifunctional hydrolase prepared according to Example 1C over 7 days. After seven days, these dosages resulted in small decreases in hemoglobin ("Hb"), red blood cell count ("RBC") and packed cell volume ("PCV"), as shown in the table below:

| Group | Dose | Sex | HB | RBC | PCV | MCV* | MCH* | MCHC* |
|---|---|---|---|---|---|---|---|---|
| 1 | 0 | M | 14.8 | 6.79 | 44.3 | 65.4 | 21.8 | 33.4 |
|   |   | F | 14.7 | 6.76 | 43.7 | 64.6 | 21.7 | 33.6 |
| 2 | 0.5 | M | 14.0 | 6.35 | 41.8 | 65.9 | 22.2 | 33.6 |
|   |   | F | 13.8 | 6.12 | 40.5 | 66.3 | 22.5 | 33.9 |
| 3 | 5 | M | 13.8 | 6.25 | 41.1 | 65.8 | 22.1 | 33.6 |
|   |   | F | 13.4 | 5.94 | 39.9 | 67.2 | 22.6 | 33.6 |
| 4 | 50 | M | 13.1 | 6.19 | 39.1 | 63.3 | 21.3 | 33.6 |
|   |   | F | 13.0 | 6.01 | 38.8 | 64.6 | 21.7 | 33.6 |

*MCV = mean corpuscular volume
MCH = mean corpuscular hemoglobin
MCHC = mean corpuscular hemoglobin concentration None of the treated animals showed any visible symptoms of illness or adverse reaction.

Example 7

Toxicity on Mice

The toxicity of poly-enzyme preparation has also been tested on mice with s.c. implanted P388 murine leukemia (a chemically induced cancer) and compared with doxorubicin, a well known anti-cancer drug (abbreviation DOX). The results are summarized in the following Table. No mouse treated with the poly-enzyme preparation of Example 1A or in the control group died or lost weight, whereas all mice in the doxorubicin group, except for those receiving the lowest dosage, lost weight and died. The highest dose of poly-enzyme preparation (20 mg/kg) was far higher than any of the doses used in the clinical examples described below.

Toxicity of poly-enzyme preparation and DOX administered i.p. daily during 9 consecutive days to mice with P388 murine leukemia

| Drug | Dose (mg/kg) | Toxic death | Body wt. chg. (g) |
|---|---|---|---|
| Control | 0 | 0/6 | +2.3 |
| Krill poly-enzyme preparation | 20 | 0/6 | +3.3 |
|  | 10 | 0/6 | +3.3 |
|  | 5 | 0/6 | +3.3 |
| DOX | 5 | 6/6 | −2.3 |
|  | 2.5 | 6/6 | −0.6 |
|  | 1.25 | 0/6 | +0.5 |

Example 8A

Infections in Post-Operative Surgical Wounds

Forty patients were included in this study and they were divided into two groups of 20 patients each, representing 41 post-operative abdominal (34) and thoracic (7) wounds. Preparations of krill multifunctional hydrolase prepared according to Example 1B (3 Casein-Units/ml), and krill poly-enzyme preparation of Example 1A (5 Casein-units/ml) were tested in each group. The enzyme solutions were prepared from the ampule-stored lyophilized preparations described in Examples 1A and 1B, which were reconstituted in saline prior to use.

The patients had an average age of 52±16 years, and included 28 males and 12 females. Enzyme preparations were applied to the wounds 2 times daily in an amount of 25 mg/treatment. Within 5 days all infections were brought to a subclinical level and all apparent signs of clinical infections were gone. No notable difference between the two preparations could be observed. There were no apparent adverse reactions.

Example 8B

Infected Wound

A 3 month old boy who had been operated on for a hydro cele och scrotal hernia developed by 10 days after surgery a serious infection at the site of the incision. The infected incision exuded pus. Parts of the incision threatened to split open after the stitches were removed. The boy was treated twice daily for 3 days with dressings which had been soaked in the poly-enzyme preparation of Example 1A (4 µg per treatment). After 3 days of treatment the infection was gone and the wound had healed.

Example 8C

Necrotic Post-Operative Wounds

Fifteen patients with necrotic wounds were treated with 3 Casein Units/ml solutions of the krill multifunction hydrolase according to Example 1B. The wounds were cleaned by rinsing prior to applying the hydrolase. Twice daily an ampoule of the dry form of the multifunctional enzyme described in Example 1B was diluted in 5 ml saline and poured onto a gauze dressing which covered the wound completely. The drained gauze was fixed to the wound by a self-adhesive semi-occlusive dressing. At every change of dressing the wound was visually inspected for erythema, oedema, bleeding, swelling, heat, exudation, pus, necrotic tissue, pain, smell, possible adverse reactions and general status of patient. The treatment was terminated when all necroses, fibrin, pus and blood clots were decomposed but for no longer than 7 days.

The patient population was heterogeneous with respect to the etiology of the wounds, i.e. scheduled operations, traumas, burns, shots and diabetes patients. All patients were treated on an outpatient basis twice a day. No adverse reaction were observed from the test preparations. The results are summarized in FIG. 12. The points indicated by "Y" symbols are for scoring of yellow fibrinous and purulent tissue. The points indicated by "B" symbols are for black necrotic tissue. And, the points indicated by "R" symbols are for granulation tissue and epithelium. Necroses, fibrin, pus, blood clots, and plaques were effectively decomposed within a week and some wounds healed within a week. Burns, shots, and post-operative wounds in diabetes-patient initially showed very poor efficacy, but at termination of the study, 7 days, the necroses were completely decomposed from underneath and what remained was only the top surfaces of the necroses, like a lid, and the wounds were partially healed within a week.

Example 9

Abscesses in Calves

Abscesses of approximately 25 to 40 ml volume were formed on the neck of each of two calves by injecting calcium-chloride solution. The abscesses were treated once daily by instillation of 10 ml of the poly-enzyme preparation of Example 1A (5 mg/ml) using a drainage tube. For each treatment, the tube was sealed to keep the enzyme solution in place for a minimum of 4 hours. Then the tube was then opened, allowing the abscess to drain. After the third treatment the drainage fluid was clear and after the sixth treatment the tubes were removed. The "pockets" healed completely after 9 and 12 days, respectively.

Example 10

Scleroderma

The patient suffered from chronic hardening and thickening of the skin, i.e., scleroderma in his fingertips on his right hand. He was treated by twice daily applying 0.5 ml of hydrogel (described in Example 1F) containing 0.5 mg/ml of the krill multifunctional hydrolase according to Example 1B. The pain associated with the condition was substantially reduced within 48 hours, and after three weeks all cracks were healed. Treatment was discontinued after three weeks. No recurrence occurred during six weeks of follow up.

Example 11

Prophylactic Treatment of Post-Surgical Wounds

Krill multifunctional hydrolase according to Example 1B (1) and krill poly-enzyme preparation of Example 1A (2) were tested against a sterile 0.9% NaCl control solution (3) as a prophylactic anti-microbial rinsing solution on post-op. wounds. Each of the treatment groups included 20 patients.

Non-bleeding post-operative wounds were treated twice daily with saline, multifunctional hydrolase (3 Casein Units/ml) or poly-enzyme preparation (5 Casein Units/ml). The wounds were rinsed thoroughly with the respective solution and covered with sterile gauze under a semi occlusive dressing. At each redressing, the wounds were inspected for infection, inflammation, erythema, swelling, heat, necrotic tissue, fibrin, pus, bleeding, pain and possible adverse reactions.

No post-operative clinical infections occurred in the groups treated with multifunctional hydrolase or poly-enzyme preparation, nor was acute inflammation or erythema observed in any of the patients in these two groups. For both groups treated with one of the enzyme compositions, 18 wounds were healed (>90% epithelialization) within 10 days treatment. No adverse reactions were observed. In the control group, 4 patients developed severe invasive infections and additional 2 patients developed acute inflammations. Erythema, swelling and pain were frequent observations in this group. In the control group, 14 wounds healed within 10 days of treatment.

Example 12

Small-Sized Burns

Eleven patients with small, full thickness burns infected by *S. aureus* and *P. aeruginosa* and who did not respond to antibiotics and silver sulfadiazine cream were included in this study. 5 patients were treated with krill multifunctional hydrolase according in a hydrocolloid cream as described in Example 1F (3 Casein-Units/ml) and 6 patients with the krill poly-enzyme preparation of Example 1A in isotonic saline solution (5 Casein-Units/ml).

Wounds were treated two times daily with 25 mg/treatment of multifunctional hydrolase. All wounds were completely free from all signs of infection within 5 days treatment. The lack of infection was confirmed by microorganism (MO) cultivation. Necrotic tissue, pus and fibrinous fibrils in the granulation tissue were effectively decomposed by both preparations and no perceptible difference in efficacy between the preparations could be observed. No adverse reactions were observed. The test results were:

used to treat anal fistulae. Prior to use, one ampoule of the multifunctional hydrolase was reconstituted in 5 ml of hydrogel to a final concentration of 3 Casein-Units/ml. The poly-enzyme preparation was reconstituted in hydrogel to a final concentration of 5 Casein-Units/ml. The fistulae were rinsed with sterile solution and emptied as far as possible, and then irrigated with hydrogel containing multifunctional hydrolase or poly-enzyme preparation. The procedure was repeated once daily and patients were inspected for erythema, heat, swelling, pus, pain and adverse reactions. The treatment continued until all signs of infection and inflammation were gone, but for no longer than 10 days. For each gel preparation, two patients with anal fistulae, with no passages to rectum, were used and treated with multifunctional hydrolase and poly-enzyme preparation, respectively. For both sets of

| Wound No./ Size (cm²) | Strain | MO-status before ($10^3$) | Visual Percentage of | | | | | Preparation | Day of termin. | MO-status after ($10^3$) | Visual percentage of | | | | | Healed day post-treatm. |
| --- | --- | --- | --- | --- | --- | --- | --- | --- | --- | --- | --- | --- | --- | --- | --- | --- |
| | | | Necr. | Pus | F/brin | Granul. | Epith. | | | | Necr. | Pus | F/brin | Granu. | Epith. | |
| I 1.5 | P. aerig. | 16 | 20 | 60 | 20 | | | Solution | 3.5 | <1 | | | | 30 | 70 | 3 |
| II 4.0 | P. aerig. | 18 | 50 | 10 | 40 | | | Gel | 5.0 | <1 | | | 10 | 60 | 30 | 11 |
| III 3.6 | S. aureus | 22 | 10 | 90 | | | | Gel | 3.0 | <1 | | | 10 | 40 | 50 | 6 |
| IV 2.4 | P. aerig. | 14 | 40 | 10 | 50 | | | Gel | 3.0 | <1 | | | | 50 | 50 | — |
| V 2.8 | S. aureus | 17 | | 100 | | | | Solution | 4.0 | <1 | | | | 30 | 70 | 7 |
| VI 1.9 | S. aureus | 16 | | 100 | | | | Solution | 2.5 | <1 | | | | 20 | 80 | 4 |
| VII 4.5 | S. aureus | 15 | 10 | 80 | 10 | | | Gel | 5.0 | <1 | | | 10 | 60 | 30 | 15 |
| VIII 3.2 | P. aerig. | 12 | 40 | 40 | 20 | | | Solution | 3.0 | <1 | | | | 60 | 40 | 6 |
| IX 1.8 | S. aureus | 16 | 10 | 90 | | | | Solution | 2.5 | <1 | | | | 20 | 80 | — |
| X 1.3 | P. airig. | 17 | 30 | 30 | 40 | | | Gel | 3.5 | <1 | | | | 40 | 60 | 8 |
| XI 3.1 | P. aerig. | 20 | 30 | 30 | 40 | | | Solution | 5.0 | <1 | | | 10 | 80 | 10 | 18 |

Example 13

Infected Decubitus Ulcera

Fourteen elderly patients with a total of 18 decubitus ulcers on their heels or lower back were included in this study. Ulcers were rinsed thoroughly with saline and emptied as much as possible and irrigated with 5 ml, krill poly-enzyme preparation of Example 1A dissolved in saline (5 Casein Units/ml). The ulcers were then covered with semi-occlusive dressing. The procedure was repeated twice daily for 7 days and ulcera were inspected for inflammation, erythema, heat, swelling, necrotic tissue, pus, pain and possible adverse reactions. Infections were gone within 4 days of treatment. Six wounds healed completely within 7 days, and a total of eleven have healed within 14 days. Seven wounds did not heal probably due to the overall condition of the patients, but the wounds showed some progress. No adverse reactions were observed.

Example 14

Fistulae Infections

Krill multifunctional hydrolase according to Example 1B and the krill poly-enzyme preparation of Example 1A were patients, total pain relief was reported within 48 hours and all signs of infections and inflammations were gone after 4 days. All fistulae were healed between day 6 and day 9, and no recurrence was reported within 6 months of follow-up. No adverse reactions were observed.

Example 15

Athlete's Foot (Epidermophytosis)

The purpose was to study the effectiveness of krill poly-enzyme preparation treating epidermophytosis of the foot. Forty-one patients with fungal infections were included in this study. Patients soaked their feet for thirty minutes once a day for three successive days in an aqueous solution contain 5 Casein Units/ml of poly-enzyme preparation of Example 1A for 30 minutes. Also, a hydrogel (described in Example 1F) containing 5 Casein Units/ml of the krill poly-enzyme preparation was applied to the affected areas each evening immediately before bedtime for 7 nights. The pain relief was instant in many patients and pain was totally gone within 2 days for others. Plaques over open surfaces, in cracks and under nails were readily removed by the poly-enzyme preparation and all signs of plaque, smell and infections were gone after three days.

Example 16A

Foreskin Infection

The foreskin infections of two infants, 4 and 6 weeks old, respectively, were treated twice daily with a solution of poly-enzyme preparation of Example 1A containing 1 Casein Unit/ml. 10 ml of the solution was flushed under the foreskin morning and evening, using a standard syringe with a soft catheter. After 3 days both the infants were free from symptoms and the infections did not recur during a 2 month follow-up.

Example 16B

Foreskin Infections in Dogs

Six dogs with foreskin infections were flushed under the prepuce once daily with a solution of poly-enzyme preparation of Example 1A containing 1 Casein Unit/ml. A soft silicone catheter attached to a syringe was inserted under the foreskin and used to slowly flush the affected area with 10 ml of the poly-enzyme solution. Approximately 1 ml of the solution was kept under the foreskin for minimum of 2 minutes and the dogs were kept from licking the affected area for 30 minutes. Purulent exudation stopped within 2 days in all the cases and all signs of infection and inflammation were gone within 4 days.

Example 17A

Opportunistic Infections

Two patients with uterine cancer in stage IV with opportunistic infections in non-healing post-operative wounds and one patient with an opportunistic infection of an irradiation wound were treated twice daily with dressings saturated with a solution of 5 mg/ml of the poly-enzyme preparation of Example 1A. The infections were believed to be bacterial infections. After 12, 14 and 17 days, respectively, the wounds had healed.

Example 17B

*Mycoplasma* Infection

A 55 years old man contracted an acute *mycoplasma* infection 3 years ago and was treated with different kinds of antibiotics. However, these treatments became ineffective when a resistant form developed. Some weeks after the infection the man contracted high fever with a very severe cough as a result and in X-ray examination water in the pleura was observed. The complaints of the man manifested themselves in the form of respiration complaints, difficulty to walk longer distances than 100 meter without a break and severe tiredness as well as annoying hacking cough.

The patient was treated with 2 mls of a 2 mg/ml solution (4 mg total) of the krill multifunctional hydrolase according to Example 1B. The wash solution was kept in the mouth for about 4 minutes and then was slowly swallowed. This treatment was repeated during the first two weeks every second day. During this time, 0.5 ml of an aerosol of the wash hydrolase solution was inhaled on a daily basis. During the first two weeks no improvement was observed but after two weeks' treatment the lymph gland on the left side of the neck swelled resulting in pain. During this time the treatment was continued 3 times (every second day). After 1.5 weeks all problems regarding the lymph nodes had disappeared and the bronchitis complaints of the patient began to subside. After further 3 weeks' treatment with mouth washes every fourth day the bronchitis complaint had completely disappeared. After this total treatment extending over 6.5 weeks the patient had recovered completely and after a short time he could walk 5 kilometers with no problems.

Example 18

Boils in Dogs

Three boxers with painful, infected and excudating/bleeding boils between the toes were treated twice daily with poly-enzyme solution. A gauze was soaked with 2 ml of a solution of poly-enzyme preparation of Example 1A (5 Casein Units/ml) and then applied over the boil. The paw was bandaged to keep the gauze fixed in place and a rubber boot was used to protect the dressing. Apparent relief from pain was observed after 1 day of treatment. The flow of exudant and blood stopped within two days. After 5 to 7 days of treatment, inflammation was substantially reduced, and after 11 to 15 days, all indications of boils were gone.

Example 19

Urinary Bladder and Urethra Infections

Figure 6:
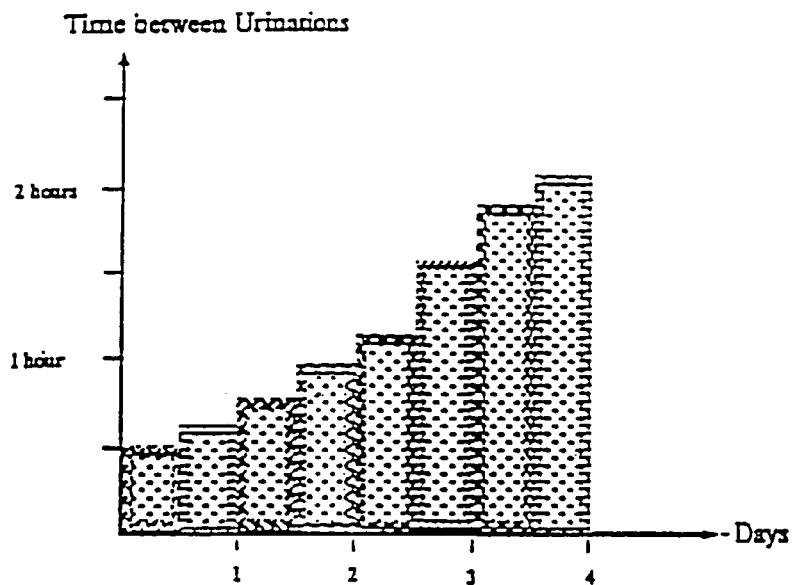
FIG. 6 shows the increase in time between urinations for urinary bladder infection patients treated with a poly-enzyme preparation of Example 1A.

Twelve female patients with painful urinary infections were included in this study. Before use, 6 ampoules of krill poly-enzyme preparation described in of Example 1A were reconstituted in 50 ml saline to a final concentration of 3 Casein-Units/ml. At the start of treatment, the first discharge of urine from all patients was very turbid and the second discharge was clear to weakly turbid. Patients were treated with 50 ml of the saline solution by instillation 2 times daily. Pain relief was instant and improved ability to retain urine was obvious after two days of treatment. Micro-organism (MO) samples confirmed no bacteria after 4 days of treatment and all treatments were terminated after 4 days. No adverse reactions were observed. The results are summarized in FIG. 6. The average MO-status values are shown in the table below.

|  | BEFORE TREATMENT | DAY 2 | DAY 4 |
|---|---|---|---|
| MO Status: (average) | $1.4 \times 10^4$ | $4.3 \times 10^4$ | $<1.0 \times 10^2$ |
| Relative MO Status: (% of initial status) | 100% | 31% | 1% |

Example 20

Eye Infections

Fifteen patients with purulent eye infections were treated twice daily with eye-drops of the poly-enzyme preparation from krill. Before use, an ampoule of poly-enzyme preparation as described in Example 1A was reconstituted in 25 ml water to a final concentration of 1 Casein-Unit/ml. The infected eye was treated morning and evening with two drops, 0.4 ml, of the solution. At each application, the eye was inspected for erythema, swelling, pus, lacrimal secretion and possible adverse reactions. The patient was treated until all signs of infection were gone, but not for longer than 10 days. All patients were free from infections within 3 days of treatment. Erythema and swelling around the eyes faded away within 2 days and excess lacrimal secretion-ceased within 2 days. After the first application all patients experienced a soothing feeling in the infected eye and irritation and tenderness around the eyes disappeared within a few minutes. No adverse reactions were reported.

Example 21

Gum Infections

Twenty-two patients with acute or chronic gum infections/inflammations were included in this study. Three times a day (morning, mid-day and evening) one of the ampoules of polyenzyme preparation described in Example 1A was reconstituted in 5 ml tap water (yielding 5 Casein units/ml) and used to rinse a patient's mouth cavity for 5 minutes. No eating and drinking within 2 hours after treatment was allowed. The treatment went on for 7 days independent of results. Pain relief was reported after 20 minutes to 12 hours of treatment. Infections and inflammations vanished within 4 days and did not reoccur during a follow-up period of 3 weeks. No adverse reactions were reported.

Example 22A

Viral Infections in the Upper Airways

Eleven patients with influenza virus infections and secondary bacterial infections in the upper airways, such as sinusitis, were included in this study. Viral infections in the lungs cause harm to lung cilia and inflammatory reactions that lead to erythema, swelling and increased mucus secretion. The harmed cilia can no longer wipe away inhaled bacteria, which often leads to secondary bacterial infections. Viruses are dependent on host-cells for their survival and multiplication and it is difficult to kill a virus without harming or killing host cells. Prior to treatment, one of the ampoules of krill multifunctional hydrolase described in Example 1B was reconstituted in 5 ml of saline to a final concentration of 5 Casein-Units per ml. 0.25 ml of this reconstituted solution was sprayed in each nostril and the mouth-cavity was rinsed for 5 minutes with 4.5 ml of the solution. The procedure was repeated three times daily and erythema, swelling, mucus-secretion, pain and adverse reactions were recorded once daily.

Figure 7:
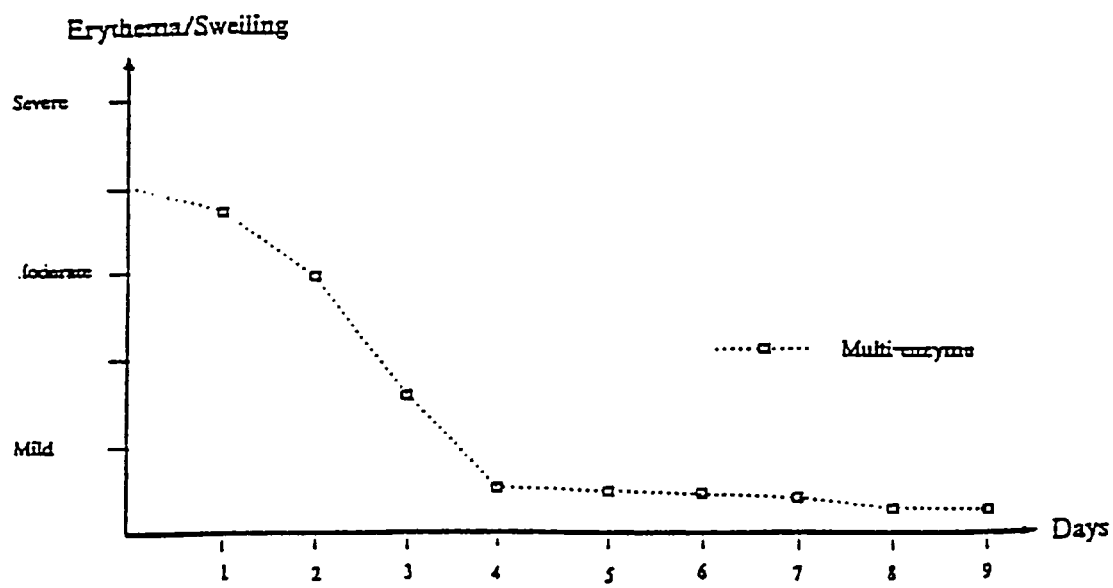
FIG. 7 shows the reduction in erythema/swelling in patients with viral lung infections treated with the multifunctional enzyme purified as described in Example 1B.

The treatment was continued until all signs of infection were gone but not for longer than 10 days. 8 patients were free from symptoms after 6 days of treatment and the remaining three patients after 9 days. Pain relief was experienced by all patients and occurred within 2 hours to two days. Sputum became clear within three days in patients with purulent discharges. Erythema and swelling disappeared within 4 days. The results are summarized in FIG. 7. No adverse reactions were observed.

Example 22B

Common Cold

Five patients in the age of from 30 to 63 years were treated with the krill multifunctional hydrolase according to Example 1B only a few hours after the outbreak of the first cold symptoms. The treatment was carried out with nasal sprays of 0.5 µg/ml aqueous solutions of the hydrolase (0.1 mg per nostril inhaled) every 4 hours and with 0.5 mg/ml mouth wash solutions (1.5 mg per wash) every 6 hours. The mouth wash solution was kept in the mouth for about 2-4 minutes and then swallowed. After 12 hours the common cold symptoms had disappeared and the patients were free of complaints.

Example 23

*Haemophilus Influenzae* Infections

A woman of 34 had recurring sinusitis caused by infection of *Haemophilus influenzae*. A few hours after the appearance of the symptoms of pressure and pain in the nasal sinus, her mouth was washed for 3 minutes with 4.5 ml of a 5 µg/ml solution of krill multifunctional hydrolase according to Example 1B and 0.5 ml of the hydrolase solution was sprayed into each of her nostrils. This combined treatment was repeated three times at 2 hour intervals. After which, the spray treatment was repeated every three hours over a total of 3 days. The pressure caused by the nasal sinus infection disappeared within a few hours after the first treatment and the flow of nasal secretions strongly increased. After 3 days of treatment the woman was free of complaints.

Example 24

Bronchitis

A 55 year old man having severe bronchitis complaints was treated. The man had respiration complaints, difficulty in walking more than 100 meters, severe tiredness, and a chronic hacking cough. His physician believed his bronchitis was caused by a mycoplasma which had first infected the patient 3 years earlier and had developed antibiotic resistance. The infection led to the formation of water in the pleura, as was verified by X-ray examination. The patient was treated with mouth washes containing 4 mg/ml saline of krill multifunctional hydrolase according to Example 1B. The hydrolase solution was kept in the mouth for about 4 minutes and then it was slowly swallowed. This treatment was repeated on every alternative day for the first two weeks of treatment. Also during this time, small amounts (0.5 ml) of an aerosol of the hydrolase solution was inhaled.

During the first two weeks no improvement was observed. After two weeks treatment the lymph gland on the left side of the patient's neck swelled, resulting in pain. Following this, the treatment was repeated about 3 times. About 1.5 weeks after this, the lymph node swelling had disappeared and the bronchitis complaints of the patient began to subside. After a further 3 weeks of treatment with mouth washes on every fourth day the bronchitis complaint had disappeared. After a treatment extending over 6.5 weeks the patient had recovered completely, and after a short time he could walk substantial distances without problems.

Example 25A

Gastric Ulcer

A man of 40 having recurring complaints characteristic of a mild form of gastric ulcer was treated with acid-resistant gelatin capsules containing 5 mg of the krill poly-enzyme preparation of Example 1A per capsule. No filler was added to the encapsulated preparation. The patient swallowed 1 capsule a day with a glass of water for 2 weeks. After about 4 days the stomach complaints disappeared and the patient's intestines functioned normally.

A 55 years old man having recurring gastric ulcer complaints over 20 years was treated with the same dosage described above. After a few day's treatment the complaints had disappeared and his intestines worked normally.

Example 25B

Colitis Ulcerative

The patient had a fifteen year medical history of Colitis Ulcerative, which had been treated with the antiphlogistic Salazopyrine (Pharmacia, Sweden). For six weeks she swallowed once daily an acid resistant capsule containing 1 mg of lyophilized, krill multifunctional hydrolase according to Example 1B. Concurrently she maintained her Salazopyrine treatment. Two hours after her first treatment with the multifunctional hydrolase, she experienced an attack of gastric pain, gas and diarrhea and these symptoms remained for approximately six hours. After her second treatment she experienced slight pain for about 30 minutes. After this, she experienced no further adverse reactions. On days 16 and 29 she experienced gastric pain and diarrhea in connection with unusual meals. However, these episodes where shorter and less severe than her previous episodes. Through the course of the treatment, she recorded improved comfort. During the 3-4 months following treatment, her symptoms slowly returned to the severity reported pre-treatment.

Example 26

Herpes Genitalis

A man of 62 having a long established case of Herpes genitalis was treated. Outbreaks recurred regularly every 4 months, and during acute outbreaks the man abstained from sexual intercourse. During an acute outbreak, the affected area was bandaged with a bandage soaked with a solution of krill multifunctional hydrolase according to Example 1B until it contained 3 mg of hydrolase. The bandaging treatment was repeated twice a day for 2 days. His complaints disappeared after the second treatment. The man had no outbreaks during the 10 months following treatment.

Example 27

Heroes Simplex Infection in the Mouth Cavity

Eight patients with relapsed herpes simplex blisters in the mouth cavity were treated twice daily with mouth-wash. Prior to use, each ampoule of krill poly-enzyme preparation (described in Example 1A) was reconstituted in 5 ml of saline to a final concentration of 5 Casein-Units/ml. The patient rinsed his or her mouth cavity with the solution for 5 minutes. No eating or drinking was allowed within 2 hours after each treatment. The procedure was repeated twice daily and clinical parameters, erythema, swelling, pain and adverse reactions were recorded once daily. The treatment was continued until all signs of infection were gone, but not for longer than 10 days.

Pain relief was experienced within 2 hours after the first treatment. In some patients the pain recurred between treatments during the first two days, but never thereafter. After 5 days, all patients were free from symptoms and all blisters had healed. No adverse reactions were observed.

Example 28

Herpes Zoster

A 70 year old man who had had a very painful herpes zoster infection in his face for 10 months was treated topically with a gauze bandage soaked to absorb a solution containing 1-2 mg of krill poly-enzyme preparation of Example 1A every three days. After the first treatment the itch and pain were reduced. The pain disappeared completely after 12 days. Due to the pain associated with the infection, the man had had difficulties in chewing, but after 12 days he was able to chew food with no problems.

Example 29

Acne

Two women, aged 29 and 30 years, were treated for facial acne. The 29 year old woman had severe acne, whereas the 30 years old woman had moderate acne. The patients were treated with 0.1 mg of krill multifunctional hydrolase according to Example 1B several times a day for 4-6 days by applying 0.5 g/cm$^2$ to 2 g/cm$^2$ of a hydrogel (described in Example 1F) containing 5 mg/ml of krill multifunctional hydrolase. Improvement was apparent after the first treatment, and after a week of treatment only pigment traces of the acne were evident.

Example 30

Psoriasis and Dry Eczema

Psoriasis plaques and dry eczema plaques were readily decomposed with hydrogel (described in Example 1F) preparations of the krill multifunctional hydrolase according to Example 1B. 0.5 g/cm$^2$ of hydrogel (described in Example 1F) containing 5 Casein Units/ml hydrolase was applied to the sites in need of treatment and the site was covered with a semi-occlusive dressing. The treatments were repeated two times daily. Within 24 hours the plaques were completely gone and the sensitive skin, especially in psoriasis patients, showed reduced inflammation. Following treatment, the affected areas were responsive to steroid creams.

Example 31A

Eczema Infections

Forty patients with eczematous seborrheic and psoriasis infections were treated once to twice daily with poly-enzyme hydrogel (described in Example 1F) containing 2.5 Casein Units/ml of the poly-enzyme preparation of Example 1A. Patients with dry eczema/plaque showed no signs of inflammation or infection after 2-4 treatments. The fatty type of seborrheic plaques disappeared after 6-9 days, though the associated inflammations/infections had vanished within the initial 2-4 days of treatment. Patients with psoriasis plaque experienced an improved responsiveness to steroid creams, probably due to removal of plaque by the poly-enzyme preparation, resulting in better access to the skin.

Example 31B

Lichen Planus

With Associated Infection

The patient suffered from lichen planus of the lower gum. The affected areas showed papules and lesions, and were covered with yeast plaque. Each day at that time 1 g of a hydrogel (described in Example 1F) containing 0.5 mg/ml of krill multifunctional hydrolase according to Example 1B was applied to the affected areas. After three days, the plaques and papules were gone. On day 7, all lesions were healed and the treatment was stopped.

Example 32

Thrombolytic/Anti-Embolic Properties

Thrombi were caused by applying an artificial stasis to the main ear vein of a rabbit until a proper thrombus had developed. krill multifunctional hydrolase according to Example 1B was injected (0.5 mg dissolved in 0.2 ml of isotonic solution), into the ear vein in the direction of the thrombus, at a location 2 cm from the ischemic area. Within 30 minutes the thrombus had completely dissolved and the blood had free passage. Small necroses developed in the treated area but these were resorbed within 7 days. In the control animals the ischemic area turned necrotic within 4-5 days.

Example 33

Dental Plague in Dogs

The krill poly-enzyme preparation was used to remove dental plaque in beagles. Before use, ampoules of the poly-enzyme preparation (described in Example 1A) were reconstituted in 5 ml of saline to a final concentration of 5 Casein-Units/ml. The content from a freshly prepared ampoule was carefully painted over teeth and gingiva. The tongue was fixated for 2 minutes and food and beverage were not allowed for 2 hours post-treatment. The treatment was repeated twice daily until all plaque was completely decomposed. The dogs were inspected for status of plaque, saliva secretion and adverse reactions once daily. Eight beagles with abnormal plaque formation due to special feeding and housing were included in this study. After 4 days all signs of plaque were gone and the study was terminated. No adverse reactions could be observed.

Example 34

Human Dental Plaque

The krill poly-enzyme preparation was used to remove dental plaque in humans. One ampoule of poly-enzyme preparation of Example 1A was reconstituted, in 5 ml of saline to a final concentration of 5 Casein-Units/ml, before each treatment and used to rinse the patient's mouth cavity for 5 minutes. Food and beverage were not allowed for 2 hours post-treatment. The treatment was repeated twice daily and the patients were inspected once daily for plaque, saliva secretion, dryness, and adverse reactions. The patients were not allowed to brush their teeth during the study period. The treatment was continued until all signs of plaque were gone, but not for longer than 7 days. Two hours after the first treatment all patients experienced a soft and smooth sense over their teeth but visual inspection showed remnants of plaque. Two hours after the third treatment, all signs of plaque were gone and treatments were terminated. No adverse reactions were observed.

Example 35

Cancer

The krill poly-enzyme preparation of Example 1A was used to treat Yoshida Sarcoma tumors in juvenile rats. Yoshida sarcoma cells are described in Micotina et al., *Tumour Biology*, 12: 225, 1991, and Goseki et al., *Cancer*, 69: 1865, 1992. The poly-enzyme preparation was administered by three different routes (intraperitoneally (i.p.), intratumorally (i.t.) and subcutaneously (s.c.)) to white Wistar rats that had been implanted Yoshida Sarcoma cells. The treatment groups were as follows:

A. A single administration i.p. of 5 mg/kg.
B. A single administration i.t. of 5 mg/kg.
C. A single administration s.c. of 5 mg/kg.
D. Twice daily administration s.c. of 1.25 mg/kg for seven days.
E. S.c. administrations of 5 mg/kg on four alternating days.
F. S.c. administrations of 12.5 mg/kg on four alternating days.

Before use, ampules of the poly-enzyme preparation powder were reconstituted in isotonic saline at a concentration of 5 mg/ml solution. $1 \times 10^4$ Yoshida Sarcoma cells were implanted subcutaneously on the back of white Wistar rats. When the implanted cells had generated a 10 mm×10 mm tumor, the rats were either treated with poly-enzyme preparation or used as untreated controls. The rats were sacrificed 7 days after the last treatment. The size of the tumors was measured and compared with the tumors of untreated control rats.

The relative reduction of the size of the tumor was 46% for group A, 56% for group B and 49% group C. In the group treated with repeated doses of 1.25 mg/kg twice a day over 7 days (group D), the reduction was 72%. In the groups receiving 5 mg/kg and 12.5 mg/kg s.c. every second day (groups E & F), the tumor reductions were 53% and 69%, respectively. In all treated rats, the portion of the tumors that was necrotic was substantially higher than for tumors from untreated rats. Also, the treated rats gained weight more rapidly than did untreated rats.

One rat in the group receiving 12.5 mg/kg every second day showed an absolute loss of tumor mass (rather than a relative loss). The degree of metastasis in the treatment groups was very small compared to the control rats. The treated rats showed normal behavior regarding drinking and eating, in contrast to the control rats, which were subdued and exhibited no appetite. No adverse reactions could be observed during this trial.

Example 36

Anti-Viral Effect on HIV-Contaminated Cell Lines, In Vitro

The krill multifunctional hydrolase was tested for anti-HIV using the National Cancer Institute's standard assay. See Weislow et al., J. Natl. Cancer Inst. 81:577-586, 1989. The procedure comprises:

(1) The multifunctional hydrolase according to Example 1C was dissolved in dimethyl sulfoxide, diluted 1:100 in cell culture medium, and then subjected to serial dilutions. Virus infected T4 lymphocytes (CEM cell line) were added to the various dilutions. Matched controls comprise uninfected cells treated with the hydrolase for HIV-infected cells parallelly treated without the presence of the multifunctional hydrolase.

(2) The cell cultures were incubated at 37° C. under 5% carbon dioxide atmosphere for 6 days.

Figure 8:
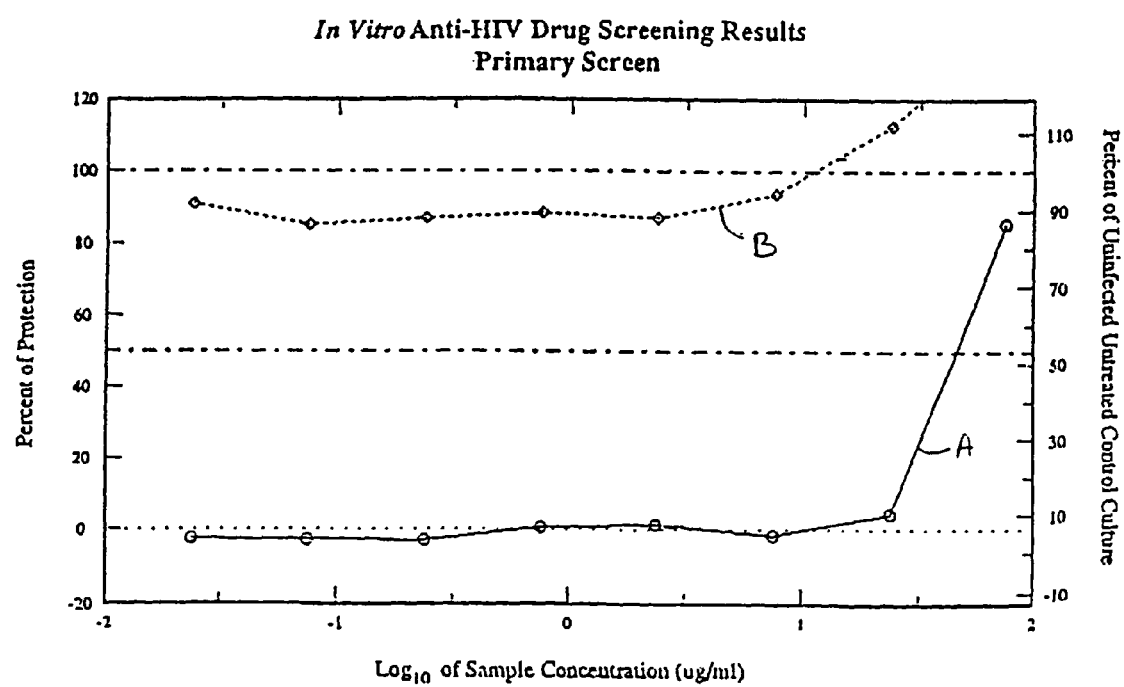
FIG. 8 shows the protective effect of the multifunctional enzyme, purified as described in Example 1C, against HIV.

(3) Tetrazolium salt, XTT, was added to the culture wells, and the cultures were incubated to allow color development by viable cells. Four of the cultures were analyzed spectrophotometrically and microscopically to quantitate the number of viable cells present. FIG. 8 shows a run of the assay. Line A is for the cells treated with multifunctional hydrolase, while Line B is the uninfected control. No activity is seen until concentrations in excess of 10 µg/ml, at which point a sharp transition in activity occurs and the hydrolase begins to show near total protective activity. The concentrations at which the hydrolase shows substantial protection are at least ten-fold less than the blood serum concentrations known to be safe.

Example 37

Grey Cataract in Dog

The right eye of a dog suffering from grey cataracts was treated with 2 drops of a 5 Casein Unit/ml solution of the poly-enzyme preparation of Example 1A. The left eye was identically treated except that a 3 Casein Unit/ml solution of the multifunctional hydrolase according to Example 1B was used. The procedure was repeated once daily for each eye and the dog was inspected for changes in opacity and adverse reactions. After 5 days an obvious diminishing in the opacity could be noted in both eyes and after 10 days both eyes looked very clear and the treatment was terminated. No adverse reactions were observed.

Example 38

Cataract in Human

A woman in her 80's with day/night vision on one eye due to gray cataract was treated every three days with 0.4 ml of solution a 0.1 mg/ml of the poly-enzyme preparation of Example 1A. After 5 treatments the study had to be terminated due to other medical reasons but an obvious reduction in opacity was observed and the lady reported improved vision on the affected eye. No irritation, pain or other discomfort could be observed during the treatment or 1 month post-treatment.

Example 39

Glaucoma

A man, age 74, experienced a slight pain/discomfort in the right eye and it was found that he suffered from an increased intraocular pressure that was found to be permanent and not caused by acute reasons. Every four days a solution containing 0.1 mg of the poly-enzyme preparation of Example 1A was dropped into the affected eye for a total of three times. Two weeks post-treatment the intraocular pressure was normal and remained normal 4 months post-treatment. The man experienced immediate pain relief, within 20 minutes, at the first treatment. No adverse reactions were observed.

Example 40

General Purpose Eye Drops

Twelve patients with no record of eye diseases, allergic reactions to air pollutants or eye infections/inflammation were treated for "tired and irritated eyes". Two drops of a 0.1 Casein Unit/ml solution of the poly-enzyme preparation of Example 1A were dropped into the eyes whenever needed. All patients experienced an alleviation of tension and pain within 30 minutes. No one reported any change in light sensitivity, focusing or any dilatation of the pupils. Occasionally a transitory dryness was experienced. No irritation, increase in lacrimal secretion or other adverse reactions were observed.

Example 41

Tendon-Sheath Adhesions

The left Achilles-tendon of each of two rabbits was ruptured and immediately sutured in a split/overlapping technique. On Day 5 post-operation, there was an evident adhesion between the tendon and the tendon sheath. One mg of the poly-enzyme preparation (of Example 1A) dissolved in 0.25 ml was injected interstitially in the sheath on Day 5, Day 7 and Day 9 post-operation. One day (24 hours) after the first injection there was no evident adhesion between tendon and sheath. Six weeks post-operation the adhesion had not recurred. Eight months post-operation the animals were sacrificed and the tendons were macroscopically inspected for adhesions, surplus of fibrin and collagen. The tendons and sheaths had healed separately and no signs of adhesions could be observed. The tensile strength of the operated left leg tendons were compared to the unoperated right leg tendons and no difference could be detected. It is believed that the preparation specifically decomposed the surplus of fibrin without affecting the fibrin needed for a proper healing of tendon and sheath, respectively.

Example 42

Detachment of an Adhered Wrist

A woman in her 40's suffered from a stiff wrist due to a long period of immobilization within a hard plaster cast. She exhibited about 25% of normal mobility. Despite a training program the mobility of the affected joint improved poorly and the diagnosis was fixation due to fibrin coating inside the joint. A solution of the poly-enzyme preparation of Example 1A was injected intraarticularly (2 mg/0.5 ml) every three days for a total of four injections. Joint mobility improved successively over 14 days to 50-60% mobility. The woman recovered a mobility to 70-80% after 4 months of rehabilitative training. No adverse reactions were observed.

Example 43

Decomposition of Scars and Keloids

A solution of the poly-enzyme preparation of Example 1A was injected once daily into 5 facial scar formations and 3 keloid formations on hands and forearms. For every centimeter of the scar/keloid 0.2 ml of the solution (containing 5 Casein Units/ml) was injected to a maximum volume of 1 ml per scar or keloid per day. The procedure was repeated once daily and the scar/keloid was inspected for erythema, swelling, heat, bleeding, necroses and adverse reactions. The treatment was terminated at 80% decomposition of scar/keloid but for no longer than 7 days. Fibrinous scars were reduced to 25% of their initial volumes and collagenous keloids to 70% after 7 days of treatment. No adverse reactions were observed during this trial.

Example 44

Wrinkle Reduction

A 33 year old woman was treated each night for 60 days by applying for 30 minutes a gauze bandage moistened with a solution of the multifunctional hydrolase according to Example 1B. The total amount of multifunction hydrolase used per application was 0.15 mg. The area below one of the patient's eyes was treated, while the other side was served as a control. After 15 days of treatment one could observe a difference in the elasticity of the skin and after 60 days of treatment there was a visually apparent difference in wrinkles. The treated skin area was very soft and elastic and the number and depth of the wrinkles had decreased considerably compared to the untreated skin area.

Example 45A

Polyps

A man of 62 having a polyp in his anus was treated. The man had suffered from the polyp for 3 years and had been treated by a physician. He had been treated with different kinds of medicines but no improvement was observed. He was treated with a gauze bandage containing about 5 mg of the multifunctional hydrolase according to Example 1B dissolved in 5 ml of saline. The treatment was repeated for a total of 5 times. All trouble disappeared and at the next visit to the physician it was observed that the polyp had disappeared. Eight months after the treatment, the man is still free of complaints.

Example 45B

Warts

A 35 years old man having a wart on his neck was treated for one week with a plaster ("Hansaplast") containing a solution of the multifunctional hydrolase according to Example 1B (0.1 mg/plaster). The treatment was repeated daily for a week. After one week's treatment, the wart had completely disappeared.

Example 45C

Hemorrhoids

Two persons were treated for hemorrhoids, a man of 55 years and a woman of 30 years. The woman had had complaints for about 3 years with pain and minor bleedings. She was treated with dry powder of the multifunctional hydrolase according to Example 1B, which was wrapped in gauze bandage that was applied onto the area concerned. Each dose was 5 mg. Five treatments were needed before the patient's complaints disappeared. She was free of complaints for one year following the treatment.

The man had been troubled with hemorrhoids off and on for a number of years. When his symptoms, including bleeding and strong pain, became acute, the man was treated once with a gauze bandage soaked with about 4 mg of the dry powder form of the multifunctional hydrolase according to Example 1B. The pain disappeared within about 20 minutes and after this single treatment all complaints disappeared and have not recurred since then.

Example 46

Treating Infection in an Infant's Navel

A 4 days old boy was treated with the multifunction hydrolase to remove necrotic tissue and to avoid upcoming infection. A gauze saturated with a solution of the multifunctional hydrolase according to Example 1B (2 mg/piece of gauze) was wound around the navel-string so that it covered both healthy, infected and necrotic navel-string tissue. The gauze bandage was changed 4 times every 12 hours. After about 12 hours, the treatment had removed the necrotic and the infected part of the tissue, whereas the healthy part of the navel-string was completely unaffected. No degradation of the healthy skin on the navel-string could be observed; neither could any infection or any skin irritation or inflammation be observed. The healthy navel was treated 4 more times. Day 6 after the birth the baby was checked at the hospital and it was found that the baby had a fine navel without any infection, in contrast to the majority of the babies who were examined on the same occasion.

Example 47

Allergic Itch

A woman, age 28, had allergic problems in the form of intense itch with nettle rashes above one of the knees and also on and below the chin. The rash exhibited white, somewhat spread elevations on the knee whereas the chin was totally spotted with small rash of the same color as the skin. A gauze bandage was wetted with a solution containing 2 mg of the krill multifunctional hydrolase according to Example 1B. The gauze was applied to the rash on the area above the knee. After 10 minutes the gauze bandage was removed. 45 minutes later the itch began to fade out and had completely disappeared after 1.5 hours. The white elevations had also disappeared and the nettle rash had faded.

One day later the area under and on the chin was treated. This area now itched intensively and was more irritated than before owing to the woman's scratching. Directly upon application of the gauze bandage with the solution of krill multifunction hydrolase, the itch increased and the gauze bandage was removed after 7 minutes owing to a very intense itch. During the following 1.5 hours the itch declined and completely disappeared after 2.95 hours. Two days after the initial treatment to the knees, no adverse reactions were observed on the treated areas.

Example 48

Prostatitis

A man of 52 years suffered from prostatitis complaints each winter since the age of 20. During the last 4 years the complaints became more acute resulting in extremely severe abdominal pain. In every acute phase he was treated with different kinds of antibiotics but as soon as the antibiotic treatment was completed, the complaints recurred within about a week. During one episode, the man received acid-resistant capsules containing 5 mg/capsule of the dry form of the multifunction hydrolase according to Example 1B. He took 2 capsules/day for a week. All symptoms disappeared and the man had no recurrence during the following 12 months.

Example 49

Mastitis (Inflammation of the Breast) in Human

A 28 years old mother of a newborn suffered severe galactostasis 3 days after delivery, the disease manifesting itself in hard, lactiferous glands and intense pain. These complaints set in half an hour after breast-feeding. She was hospitalized and treated with the standard methods available, but nothing helped. A solution containing 0.1 mg of the krill multifunction hydrolase according to Example 1B was dropped onto the nipple of the woman when the intense pain began. All pains disappeared within about 15 minutes and after about 45 minutes the hard lactiferous glands had become soft. This treatment was repeated after each breast-feeding for more than 3 months. To check the continuing need for the treatment, the woman occasionally refrained from treatment directly after breast-feeding. Each time this check was made the intense pains and the hard lactiferous glands recurred.

Example 50

Inflamed Joints in Horse 16 lame trotters with inflamed foreleg knees were included in this study. Ampules of the poly-enzyme preparation of Example 1A were reconstituted in 10 ml water for injection at a final concentration of 2.5 Casein-Units/ml solution and 2 ml of the was injected into the painful joints of the trotters on Day 1, 2, 4 and 7. After the injections, the horses were observed for any adverse reactions or deteriorations in general condition. Clinical parameters were observed once daily. Nine cases responded with pain relief within 30 minutes to 2 hours after the first treatment, four more cases responded within 6 hours, and two more cases within 2 hours after the second injection. One case showed pain relief after the third injection and this case had an extreme swelling over the knee. Heat and swelling were reduced rapidly and no signs of inflammation could be observed after two days for 15 of the cases. No adverse reactions were observed. The averaged results are summarized in FIG. 11. One week post-treatment the horses were back on easy training.

Example 51

Tourist Diarrhoea

A 41 years old man acutely developed food poisoning (probably from *Staphylococcus*) with diarrhoea and vomiting. One hour after the man had fallen ill he was treated with a solution containing 5 mg of the krill multifunction hydrolase according to Example 1B by keeping it in the mouth for about 3 minutes, whereupon it was slowly swallowed. This procedure was repeated 3 times every other hour. After the fourth treatment the stomach pains had disappeared and the vomiting and severe diarrhoea had ended.

Example 52

Hair Thinness

Two men, 55 years old and 62 years old, respectively, were treated. They both had suffered from hair thinness for the last 10 years. The treatment was carried out by soaking the entire scalp with a solution containing 5 mg of the krill multifunction hydrolase according to Example 1B. To maintain the humidity in the scalp, it was covered with a shower cap for 30 minutes. The treatment was repeated once a week for about 3 months. After this time of treatment fresh hair began to grow out.

Example 53

Treatments with Non-Krill Enzymes

For each of Examples 8-52, the krill-derived multifunctional hydrolase is substituted with the multifunctional enzyme from another source and is comparably effective.

What is claimed is:

1. A method of removing dental plaque in mammals comprising the step of contacting the dental plaque with an effective amount of a hydrolytic enzyme composition comprising a mixture of enzymes isolated from Antarctic krill.

2. The method of claim 1, wherein the enzyme composition has endo-peptidase and exo-peptidase activities.

3. The method of claim 1, wherein the enzyme composition has at least two endo-peptidase activities and an exo-peptidase activity.

4. The method of claim 1, wherein the enzyme composition comprises enzymes having molecular weights between about 24 kd and about 34 kd as determined by SDS PAGE.

5. The method of claim 3, wherein the enzyme composition has at least three proteolytic activities selected from the group consisting of chymotrypsin activity, trypsin activity, collagenase activity and elastase activity.

6. The method of claim 3, wherein the enzyme composition has each of chymotrypsin activity, trypsin activity, collagenase activity and elastase activity.

7. The method of claim 1, wherein the mixture of enzymes is isolated from krill of a genus selected from *Euphausia* and *Thysanoessa*.

8. The method of claim 1, wherein the enzyme composition has a purity of at least about 95% with respect to macromolecules.

9. The method of claim 1, wherein the enzyme composition comprises enzymes having a molecular weight between about 20 kd and about 40 kd, as determined by SDS PAGE.

10. The method of claim 1, wherein the enzyme composition comprises a multifunctional enzyme.

11. The method of claim 10, wherein the multifunctional enzyme has at least one of a chymotrypsin, trypsin, collagenase, elastase or exo-peptidase activity.

12. The method of claim 11, wherein the multifunctional enzyme has at least two activities selected from the group consisting of chymotrypsin, activity, trypsin activity, collagenase activity, elastase activity and exo-peptidase activity.

13. The method of claim 1, wherein the enzyme composition comprises an enzyme which has an N-terminal sequence comprising IVGGM/NEVTPHAYPWQVGLFIDDMYF (SEQ ID NO: 17).

14. The method of claim 11, wherein the multifunctional enzyme has a molecular weight between about 26 kd and about 32 kd as determined by SDS PAGE.

15. A method of removing dental plaque in a mammal comprising: contacting the dental plaque with an effective amount of a poly-enzyme composition comprising enzymes isolated from Antarctic krill, and wherein said poly-enzyme composition comprises at least six proteins.

16. The method of claim 15, wherein the enzyme composition has endo- and exo-peptidase activities.

17. The method of claim 15, wherein the enzyme composition comprises enzymes having molecular weights between about 24 kd and about 34 kd as determined by SDS PAGE.

18. The method of claim 1, wherein the enzyme composition comprises a pharmaceutically acceptable topical carrier.

19. The method of claim 1, wherein the enzyme composition comprises a pharmaceutically acceptable carrier.

20. The method of claim 1, where the enzymes are isolated from Antarctic krill of the genus *Euphausia*.

* * * * *